United States Patent [19]
Brooks et al.

[11] Patent Number: 5,112,848
[45] Date of Patent: May 12, 1992

[54] FURAN AND PYRROLE CONTAINING LIPOXYGENASE INHIBITING COMPOUNDS

[75] Inventors: Dee W. Brooks, Libertyville, Ill.; Bruce P. Gunn, Saraland, Ala.; James H. Holms, Gurnee; James B. Summers, Libertyville, both of Ill.

[73] Assignee: Abbott Laboratories, Abbott Park, Ill.

[21] Appl. No.: 487,982

[22] PCT Filed: Nov. 14, 1988

[86] PCT No.: PCT/US88/04048
§ 371 Date: Apr. 19, 1990
§ 102(e) Date: Apr. 19, 1990

[51] Int. Cl.$^5$ ............... A61K 31/40; C07D 307/02; C07D 207/00

[52] U.S. Cl. .................. 514/424; 514/422; 514/425; 514/473; 514/408; 548/541; 548/543; 548/544; 548/545; 548/546; 549/478; 549/493; 549/494

[58] Field of Search ............ 548/541, 542, 550, 561, 548/543–546; 549/474, 478, 493, , 494; 514/422, 424, 427, 461, 473

[56] References Cited

U.S. PATENT DOCUMENTS

| 3,664,397 | 2/1972 | Raines et al. | 548/561 |
| 3,982,922 | 9/1976 | Krenzer et al. | 514/471 |
| 4,185,020 | 1/1980 | White et al. | 549/491 |
| 4,717,413 | 1/1988 | Baker et al. | 549/493 |

FOREIGN PATENT DOCUMENTS

| 0196184 | 1/1986 | European Pat. Off. | 564/347 |
| 0248594 | 9/1987 | European Pat. Off. | 548/252 |

OTHER PUBLICATIONS

Niyagishima et al., *Chem. Pharm. Bull.,* vol. 22(10) pp. 2283–2287, 1974.

*Primary Examiner*—C. Warren Ivy
*Assistant Examiner*—Celia Chang
*Attorney, Agent, or Firm*—Jerry F. Janssen

[57] ABSTRACT

Substituted furan and pyrrole compounds which are useful in inhibiting lipoxygenase enzymes, particularly 5-lipoxygenase.

10 Claims, No Drawings

FURAN AND PYRROLE CONTAINING LIPOXYGENASE INHIBITING COMPOUNDS

TECHNICAL FIELD

This invention relates to organic compounds which inhibit lipoxygenase enzymes. It also relates to methods and compositions for inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs).

Similarly, 12- and 15-lipoxygenase, convert arachidonic acid to 12- and 15-HPETE, respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs C4 and D4 are potent constrictors of human airways in vitro, and aerosol administration of these substances to non-asthmatic volunteers induces broncho-constriction. LTB4 and 5-HETE are potent chemotactic factors for inflammatory cells such as polymorphonuclear leukocytes. They also have been found in the synovial fluid of rheumatoid arthritic patients. Leukotrienes have also been implicated as important mediators in allergic rhinitis, psoriasis, adult respiratory distress syndrome, Crohn's disease, inflammatory bowel disease, endotoxin shock, and ischemia induced myocardial injury among others. The biological activity of the LTs has been reviewed by Lewis and Austen (J. Clinical Invest. 73, 889, 1984 and by J. Sirois (Adv. Lipid Res. 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes are believed to play an important role in the biosynthesis of mediators of asthma, allergy, arthritis, psoriasis, and inflammation. Blocking these enzymes interrupts the biochemical pathways believed to be involved in these disease states.

DETAILED DESCRIPTION OF THE INVENTION

In accordance with the present invention there are 5- and/or 12-lipoxygenase inhibiting compounds of the formula:

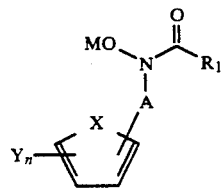

Formula I wherein
$R_1$ is hydrogen, $C_1$ to $C_4$ alkyl, $C_2$ to $C_4$ alkenyl, or $-NR_2R_3$, wherein $R_2$ and $R_3$ are independently selected from hydrogen, $C_1$ to $C_4$ alkyl, hydroxyl, aryl or substituted aryl wherein substituents are selected from halo, nitro, cyano, $C_1$ to $C_{12}$ alkyl, alkoxy, halosubstituted alkyl, alkoxycarbonyl, aminocarbonyl, alkylaminocarbonyl, dialkylaminocarbonyl and alkylsulfonyl; with the proviso that $R_2$ and $R_3$ are not both hydroxyl;

X is oxygen, or $NR_4$ wherein $R_4$ is hydrogen, $C_1$ to $C_6$ alkyl, $C_1$ to $C_6$ alkoyl, arylalkyl or aroyl;

A is selected from $C_1$ to $C_6$ alkylene and $C_2$ to $C_6$ alkenylene;

n is 0,1,2 or 3;

Y is selected independently at each occurrence from hydrogen, halogen, hydroxy, cyano, halosubstituted alkyl, $C_1$ to $C_{12}$ alkyl, $C_2$ to $C_{12}$ alkenyl, $C_1$ to $C_{12}$ alkoxy, $C_3$ to $C_8$ cycloalkyl, aryl, aryloxy, aroyl, $C_1$ to $C_{12}$ arylalkyl, $C_2$ to $C_{12}$ arylalkenyl, $C_1$ to $C_{12}$ arylalkoxy, $C_1$ to $C_{12}$ arylthioalkoxy, alkoxycarbonyl, arylalkoxycarbonyl, aminocarbonyl, alkylaminocarbonyl, dialkylaminocarbonyl, arylalkylamino, arylalkylaminocarbonyl, alkoxyalkoxyalkyl, alkoxyalkyl, arylalkoxyalkyl, arylathioalkoxyalkyl and substituted derivatives of aryl, aryloxy, aroyl, $C_1$ to $C_{12}$ arylalkyl, $C_2$ to $C_{12}$ arylalkenyl, $C_1$ to $C_{12}$ arylalkoxy, $C_1$ to $C_{12}$ arylthioalkoxy, arylalkoxyalkyl or arylthioalkoxyalkyl wherein substituents are selected from halo, nitro, cyano, $C_1$ to $C_{12}$ alkyl, alkoxy and halosubstituted alkyl;

and M is hydrogen, a pharmaceutically acceptable cation, aroyl, or $C_1$ to $C_{12}$ alkoyl.

The substituent(s) Y can be substituted at any of the positions on the aromatic ring.

Examples of compounds which are themselves within the scope of the present invention include, but are not limited to, the following:

N-hydroxy-N-(1-(5-methylfur-2-yl)ethyl) urea;
N-hydroxy-N-(1-(5-phenylfur-2-yl-)ethyl) urea;
N-hydroxy-N-(1-(5-phenylfur-2-yl)-ethyl)-N'-methyl urea;
N-hydroxy-N-(1-(5-phenylfur-2-yl)ethyl) acetamide;
N-hydroxy-N-(1-(5-(2-phenylethenyl)fur-2-yl)ethyl) urea;
N-hydroxy-N-(1-(5-(2-phenylethenyl)fur-2-yl)ethyl) N'-methyl urea;
N-hydroxy-N-(1-fur-2-ylethyl) propionamide;
N-hydroxy-N-(1-(1-methyl-5-phenylpyrrol-2-yl)ethyl)-N'-methyl urea;
N-hydroxy-N-(3-fur-2-ylprop-2-enyl) urea;
N-hydroxy-N-fur-3-ylmethyl urea;
N-hydroxy-N-(fur-3-ylmethyl)-N'-methyl urea;
N-hydroxy-N-(5-(2,4,6-trimethylphenyl)-fur-2-ylethyl) urea;
N-hydroxy-N-(1-(5-butylfur-2-yl)ethyl) urea;
N-hydroxy-N-(1-(5-phenylmethylfur-2-yl)ethyl) urea;
N-hydroxy-N-(1-(5-ethylfur-2-yl)ethyl)-methylpropionamide;
N-hydroxy-N-(1-(3,4-dimethylfur-2-yl)ethyl) propenamide;
N-hydroxy-N-(1-(3-methylfur-2-yl)ethyl) N',N'-dimethylurea;
N,N'-dihydroxy-N-(1-(5-methylfur-2-yl)ethyl) urea;
N-hydroxy-N-(2-fur-2-ylethyl) urea;
N-hydroxy-N-(1-methyl-1-fur-2-ylethyl) urea;
N-hydroxy-N-(pyrrol-2-ylmethyl) urea;
N-hydroxy-N-(5-methoxy-(1-fur-2-yl)ethyl) urea;
N-hydroxy-N-(5-fluoro-(1-fur-2-yl)ethyl) urea;
N-hydroxy-N-(3-trifluoromethyl-(1-fur-2-yl)ethyl) urea;

N-hydroxy-N-(5-phenylmethoxy-(1-fur-2-yl)ethyl) urea;
N-hydroxy-N-(4-benzoyl-(1-fur-2-yl)ethyl) urea;
N-hydroxy-N-(1-acetoxy-(1-pyrrol-2-yl)ethyl) urea;
N-hydroxy-N-(1-benzoyl-(1-pyrrol-2-yl)ethyl) urea;
N-hydroxy-N-(1-(5-(4-fluorophenylfur-2-yl)ethyl) urea;
N-hydroxy-N-(1-(5-(3,5-dimethoxyphenylmethylfur-2-yl)ethyl) urea;
N-hydroxy-N-(3-hydroxy-(1-fur-2-yl)ethyl) urea;
N-hydroxy-N-(1-(5-methylfur-2-yl)ethyl) urea sodium salt;
N-hydroxy-N-(1-(5-methylfur-2-yl)ethyl) urea ammonium salt;
N-hydroxy-N-(1-(5-methylfur-2-yl)ethyl) urea tetrabutylammonium salt;
N-butyroxy-N-(1-(5-methylfur-2-yl)ethyl) urea;
N-hydroxy-N-(1-fur 2-ylethyl) urea;
N-hydroxy-N-(5-methylfur-2-ylmethyl) urea;
N-hydroxy-N-(5-methylfur-2-yl)methyl-N'-methyl urea;
N-hydroxy-N-(1-(5-methylfur-2-yl)ethyl)-N'-phenyl urea;
N-hydroxy-N-(1-(5-methylfur-2-yl)ethyl)-N'-(4-carboethoxyphenyl) urea;
N-hydroxy-N-(1-(5-methylfur-2-yl)ethyl)-N'-(4-carboxamidophenyl) urea;
N-hydroxy-N-(1-(5-methylfur-2-yl)ethyl)-4-methylsulfonylbenzamide;
N-hydroxy-N-(1-(5-carbomethoxyfur-2-yl)ethyl) urea;
N-hydroxy-N-(1-(5-carboethoxyfur-2-yl)ethyl) urea;
N-hydroxy-N-(1-(5-N,N-diethylcarboxamidofur-2-yl)ethyl) urea;
N-hydroxy-N-(1-(5-N-benzylcarboxamidofur-2-yl)ethyl) urea;
N-hydroxy-N-(1-(5-methoxyethoxymethylfur-2-yl)ethyl) urea;
N-hydroxy-N-(1-(5-ethoxymethylfur-2-yl)methyl) urea;
N-hydroxy-N-(1-(5-benzyloxymethylfur-2-yl)ethyl) urea;
N-hydroxy-N-(1-(5-phenylfur-2-yl)methyl) urea;
N-hydroxy-N-(5-phenylfur-2-yl)methyl-N'-methyl urea;
N-hydroxy-N-(3-(fur-3-ylprop-2-enyl) urea;
N-hydroxy-N-(3-(5-phenylfur-2-yl))prop-2-enyl) urea;
N-hydroxy-N-(2,5-dimethylfur-3-ylmethyl) urea;
N-hydroxy-N-(1-(2,5-dimethyl)fur-3-yl)ethyl) urea;
N-hydroxy-N-(1-fur-3-yl)ethyl) urea;
N-hydroxy-N-(1-(5-pyrid-2-ylfur-2-yl)ethyl) urea;
N-hydroxy-N-(3-(5-methylfur-2-yl)prop-2-enyl) urea;
N-hydroxy-N-(fur-2-ylmethyl) urea; and
N-hydroxy-N-((1-methyl)-3-(5-methylfur-2-yl)prop-2-enyl) urea.

Preferred compounds of the invention include:
N-hydroxy-N-(1-(5-methylfur-2-yl)ethyl) urea;
N-hydroxy-N-(1-(5-phenylfur-2-yl)ethyl) urea;
N-hydroxy-N-(1-(5-phenylfur-2-yl)ethyl)-N'-methyl urea;
N-hydroxy-N-(1-(5-phenylfur-2-yl)ethyl) acetamide;
N-hydroxy-N-(1-(5-(2-phenylethenyl)fur-2-yl)ethyl) urea;
N-hydroxy-N-(1-(5-(2-phenylethenyl)fur-2-yl)ethyl)-N'-methyl urea;
N-hydroxy-N-(5-(2,4,6-trimethoxyphenyl)-fur-2ylethyl) urea;
N-hydroxy-N-(1-fur-2-ylethyl)urea;
N-hydroxy-N-(1-(5-carbomethoxyfur-2-yl)ethyl) urea;
N-hydroxy-N-(1-(5-benzyloxymethylfur-2-yl)ethyl) urea;
N-hydroxy-N-(5-phenylfur-2-ylmethyl) urea;
N-hydroxy-N-(3-fur-3-ylprop-2-enyl) urea
N-hydroxy-N-(3-(5-phenylfur-2-yl)prop-2-enyl) urea;
N-hydroxy-N-(1-(2,5-dimethylfur-3-yl)ethyl) urea;
N-hydroxy-N-(1-fur-3-ylethyl) urea;
N-hydroxy-N-(1-(5-pyrid-2-ylfur-2-yl)ethyl) urea;
N-hydroxy-N-3-(1-(5-methylfur-2-yl)propenyl) urea; and
N-hydroxy-N-((1-methyl)-3-(5-methylfur-2-yl)prop-2-enyl) urea.

Most preferred compounds of the invention include:
N-hydroxy-N-(1-(5-methylfur-2-yl)ethyl) urea;
N-hydroxy-N-(1-(5-phenylfur-2-yl)ethyl) urea;
N-hydroxy-N-(1-(5-phenylfur-2-yl)ethyl)-N'-methyl urea;
N-hydroxy-N-(1-(5 phenylfur-2-yl)ethyl) acetamide;
N-hydroxy-N-(1-(5-(2-phenylethenyl)fur-2-yl)ethyl) urea;
N-hydroxy-N-(1-(5-(2-phenylethenyl)fur-2-yl)ethyl)-N'-methyl urea;
N-hydroxy-N-(5-(2,4,6-trimethoxyphenyl)-fur-2-ylethyl) urea;
N-hydroxy-N-(1-(5-benzyloxymethylfur-2-yl-)ethyl) urea;
N-hydroxy-N-(5-phenylfur-2-ylmethyl) urea;
N-hydroxy-N-(3-fur-3-ylprop-2-enyl) urea
N-hydroxy-N-(3-(5-phenylfur-2-yl)prop-2-enyl) urea;
N-hydroxy-N-(1-fur-3-ylethyl) urea;
N-hydroxy-N-(1-(5-pyrid-2-ylfur-2-yl)ethyl) urea;
N-hydroxy-N-3-(1-(5-methylfur-2-yl)propenyl) urea; and
N-hydroxy-N-((1-methyl)-3-(5-methylfur-2-yl)prop-2-enyl) urea.

The term "alkylene" is used herein to mean straight or branched chain spacer radicals such as —$CH_2$—, —$CH(CH_3)$—, —$C(CH_3)_2$—, —$CH(C_2H_5)$—, —$CH_2CH_2$—, —$CH_2CH(CH_3)$—, —$C(CH_3)_2C(CH_3)_2$—, —$CH_2CH_2CH_2$— and the like.

The term "alkenylene" is used herein to mean straight or branched chain unsaturated spacer radicals wherein the unsaturation comprises a carbon-carbon double bond, such as —CH=CH—, —CH=CHCH$_2$—, —CH=CHCH(CH$_3$)—, —C(CH$_3$)=CHCH$_2$—, —CH$_2$CH=CHCH$_2$—, —C(CH$_3$)$_2$CH=CHC(CH$_3$)$_2$—, and the like.

The term "alkyl" is used herein to mean straight or branched chain radicals of 1 to 12 carbon atoms, including, but not limited to methyl, ethyl, n-propyl, isopropyl, n-butyl, sec-butyl, isobutyl, tert-butyl, and the like.

The term "alkenyl" is used herein to mean straight or branched chain unsaturated radicals of 2 to 12 carbon atoms, including, but not limited to ethenyl, 1-propenyl, 2-propenyl, 2-methyl-1-propenyl, 1-butenyl, 2-butenyl, and the like.

The term "cycloalkyl" is used herein to mean carbocyclic radicals, preferably of 3 to 8 carbons, including, but not limited to cyclopropyl, cyclobutyl, cyclopentyl, cyclohexyl, and the like.

The term "alkoxy" is used herein to mean —$OR_{15}$ wherein $R_{15}$ is an alkyl radical, including, but not limited to methoxy, ethoxy, isopropoxy, n-butoxy, sec-butoxy, isobutoxy, tert-butoxy, and the like.

The term "alkoyl" is used herein to mean —$COR_{16}$ wherein $R_{16}$ is an alkyl radical, including, but not limited to formyl, acetyl, propionyl, butyryl, isobutyryl, pivaloyl, and the like.

The term "alkoxycarbonyl" is used herein to mean —$C(O)R_{17}$ wherein $R_{17}$ is an alkoxy radical, including, but not limited to carbomethoxy, carboethoxy, carboisopropoxy, carbobutoxy, carbosec-butoxy, carboisobutoxy, carbotert-butoxy, and the like.

The term "aryl" is used herein to mean substituted and unsubstituted aromatic carbocyclic radicals and substituted and unsubstituted heterocyclic aromatic radicals wherein the substituents are selected from halo, nitro, cyano, $C_1$ to $C_{12}$ alkyl, alkoxy, halosubstituted alkyl, alkoxycarbonyl, aminocarbonyl, alkylaminocarbonyl, dialkylaminocarbonyl and alkylsulfonyl including, but not limited to, phenyl, 1-naphthyl or 2-naphthyl, fluorenyl, pyridyl, quinolyl, thienyl, thiazolyl, pyrimidyl, indolyl and the like.

The term "heterocyclic aromatic" is used herein to refer to 5 and 6 membered aromatic rings having in the ring one, two or three heteroatoms selected from N, O and S; and also including benzo fused analogs of these 5 and 6 membered heterocyclic aromatic rings including, but not limited to, pyridyl, quinolyl, furyl, benzofuryl, thienyl-, thiazolyl, pyrimidyl, indolyl and the like.

The term "aroyl" is used herein to mean —$C(O)R_{18}$ wherein $R_{18}$ is an aryl radical, including, but not limited to benzoyl, 1-naphthoyl, 2-naphthoyl, and the like.

The term "aryloxy" is used herein to mean —$OR_{19}$ wherein $R_{19}$ is an aryl radical, including, but not limited to phenoxy, 1-naphthoxy, 2-naphthoxy and the like.

The term "arylalkoxy" is used herein to mean —$OR_{20}$ wherein $R_{20}$ is an arylalkyl radical, including, but not limited to phenylmethoxy (i.e., benzyloxy), 4-fluorobenzyloxy, 1-phenylethoxy, 2-phenylethoxy, diphenylmethoxy, 1-naphthyl-methyloxy, 2-napthylmethyloxy, 9-fluorenoxy, 2-, 3- or 4-pyridylmethoxy, 2-, 3-, 4-, 5-, 6-, 7- , 8-quinolylmethoxy and the like.

The term "arylthioalkoxy" is used herein to mean —$SR_{21}$ wherein $R_{21}$ is an arylalkyl radical, including, but not limited to phenylthiomethoxy (i.e., thiobenzyloxy), 4- fluorothiobenzyloxy, 1-phenylthioethoxy, 2-phenylthioethoxy, diphenylthiomethoxy, 1-naphthylthiomethoxy and the like.

The term "arylalkyl" is used herein to mean an aryl group appended to an alkyl radical, including, but not limited to phenylmethyl (benzyl), 1-phenylethyl, 2-phenylethyl, 1-naphthylethyl and the like.

The term "arylalkenyl" is used herein to mean an aryl group appended to an alkenyl radical, including, but not limited to phenylethenyl, 3-phenylprop-1-enyl, 3- phenylprop-2-enyl, 1-naphthylethenyl and the like.

The terms "halo" and "halogen" are used herein to mean radicals derived from the elements fluorine, chlorine, bromine, or iodine.

The term "halosubstituted alkyl" refers to an alkyl radical as described above substituted with one or more halogens including, but not limited to, chloromethyl, trifluoromethyl, 2,2,2-trichloroethyl, and the like.

The term "arylalkoxycarbonyl" is used herein to refer to $R_{22}C(O)$— wherein $R_{22}$ is an arylalkoxy group.

The term "aminocarbonyl" is used herein to refer to —$C(O)NH_2$.

The term "alkylaminocarbonyl" is used herein to refer to —$C(O)NHR_{23}$ wherein $R_{23}$ is an alkyl group.

The term "dialkylaminocarbonyl" is used herein to refer to —$C(O)NR_{24}R_{25}$ wherein $R_{24}$ and $R_{25}$ are independently selected from alkyl.

The term "arylalkylamino" as used herein refers to $R_{26}NH$— wherein $R_{26}$ is an arylalkyl group.

The term "alkoxyalkoxyalkyl" is used herein to refer to an alkoxy group appended to an alkoxy group which is itself appended to an alkyl radical including, but not limited to methoxyethoxymethyl, ethoxyethoxymethyl and the like.

The term "alkoxyalkyl" is used herein to refer to an alkoxy group appended to an alkyl radical including, but not limited to, methoxymethyl, ethoxymethyl and the like.

The term "arylalkoxyalkyl" is used herein to refer to an arylalkoxy group appended to an alkyl radical including, but not limited to, benzyloxymethyl, naphthylmethyloxymethyl and the like.

The term "alkylsulfonyl" is used herein refers to $R_{27}SO_2$— wherein $R_{27}$ is an alkyl group.

The term "arylalkylaminocarbonyl" is used herein to refer to $R_{28}C(O)$— wherein $R_{28}$ is an arylalkylamino group.

The term "pharmaceutically acceptable cation" refers to non-toxic cations including but not limited to cations based on the alkali and alkaline earth metals, such as sodium, lithium, potassium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "lipoxygenase" is used herein to mean 5- and/or 12-lipoxygenase.

The compounds of the invention inhibit lipoxygenase, which makes the compounds useful in the treatment and prevention of disease states wherein lipoxygenase may be involved, including, but not limited to, asthma, rheumatoid arthritis, gout, psoriasis, allergic rhinitis, adult respiratory distress syndrome, Crohn's disease, endotoxin shock, inflammatory bowel disease and/or ischemia induced myocardial or brain injury.

Method of Treatment

This invention also provides a method of treatment for inhibiting 5- and/or 12-lipoxygenase activity in a human or lower animal host in need of such treatment which method comprises administration to the human or lower animal host of a compound of the invention in a therapeutically effective amount to inhibit lipoxygenase activity in the host. This invention also provides a method of treating asthma, rheumatoid arthritis, gout, psoriasis, allergic rhinitis, adult respiratory distress syndrome, Crohn's disease, inflammatory bowel disease, endotoxin shock, and/or ischemia-induced myocardial injury in a human or lower animal in need of such treatment comprising administering to the human or lower animal a therapeutically effective amount of a compound described above. Further, this invention also provides a method of treating or preventing the symptoms of the disease states mentioned above.

The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Formulation of Pharmaceutical Composition

This invention also provides for compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipient such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

Synthesis of the Compounds

Several synthetic methods may be used to prepare compounds of this invention. Some of these methods are described by schemes 1-5 below. Although in each case the sequence is illustrated with a compound of formula I wherein $R_1$ is methyl or $NH_2$, A is —CH(CH$_3$)—, X is oxygen and Y is hydrogen, it will be seen from the examples that other compounds of this invention can be prepared in the same manner using the appropriate starting materials. Compounds of formula I wherein $R_1$ is $CH_3$ can be prepared as described in scheme 1.

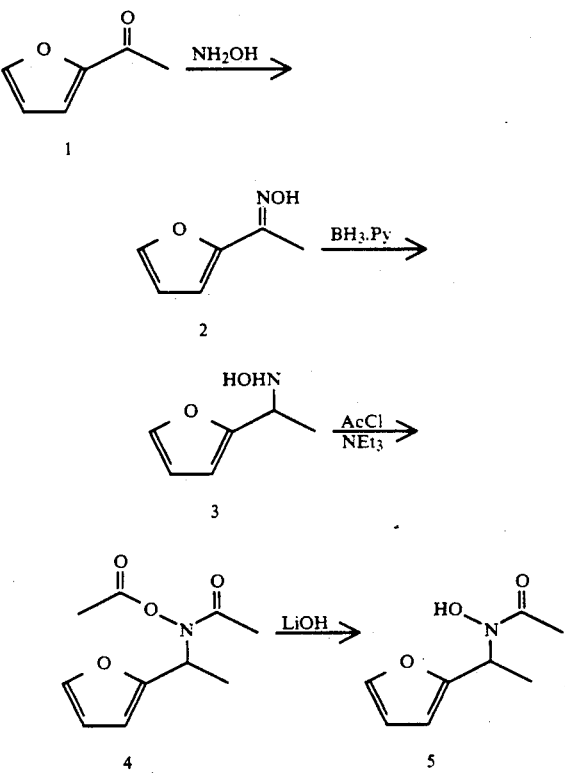

Scheme 1

In scheme 1, 2-acetylfuran 1 is treated with hydroxyl amine in ethanol/pyridine to produce the oxime 2. This is reduced to the hydroxylamine 3 with borane pyridine complex and then converted to the N,O-diacetate 4 with acetyl chloride and triethylamine. The diacetate is converted to the hydroxamic acid 5 by hydrolysis with lithium hydroxide.

Other reagents can also be used to carry out the same transformation. For example, 2 can be converted to 3 using borane trimethyl amine, borane-tetrahydrofuran, or other borane complexes. Intermediate 2 can also be converted to 3 with sodium cyanoborohydride or with phenyldimethylsilane in trifluoroacetic acid. Hydroxylamine 3 can also be converted to 4 with acylating agents such as acetic anhydride in the presence of other bases such as pyridine.

Compounds of formula I wherein $R_1$ is —$NR_2R_3$ can be prepared according to the method outlined in scheme 2, below.

Scheme 2

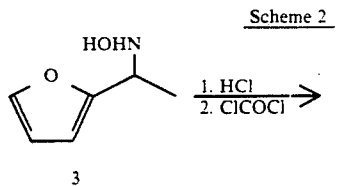
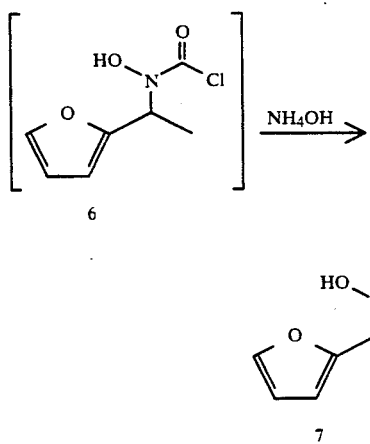

Hydroxylamine 3, the synthesis of which was described above, is treated with gaseous HCl followed by phosgene. The resulting putative carbamoyl chloride 6 is reacted without isolation with aqueous ammonia to yield the urea 7.

Compounds of formula I, wherein $R_1$ is $-NR_2R_3$ and wherein at least one of either $R_2$ or $R_3$ is hydrogen can also be prepared according to Scheme 3, below.

Scheme 3

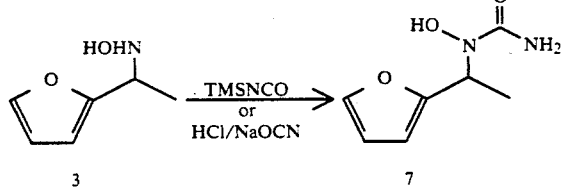

Hydroxylamine 3 is treated with trimethylsilyl isocyanate (TMSNCO), followed by ammonium chloride workup to give the urea 7. Alternatively, 3 can be treated with sodium or potassium cyanate in an acidic solution to yield the urea 7.

In addition to the methods described above, hydroxylamines such as 3 can be prepared as shown in scheme 4, below.

Scheme 4

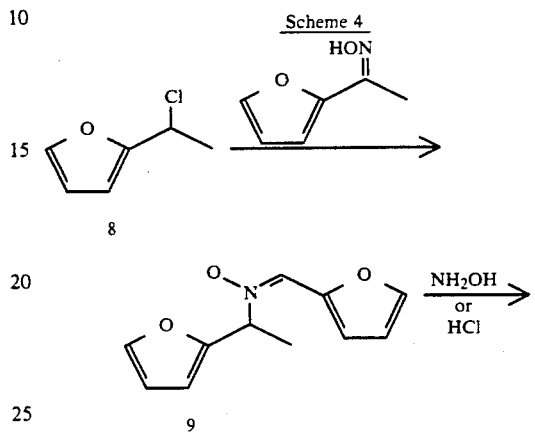
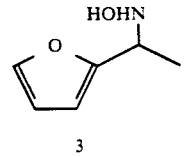

Chloride 8 is treated with Z-furfuraldehyde oxime and a base such as sodium methoxide to give nitrone 9. The nitrone is then hydrolyzed under acidic conditions or with hydroxylamine. The hydroxyl amine can be converted to compounds such as 5 and 7 using the methodology described above. Compounds with other leaving groups such as bromides, iodides, tosylates, mesylates, triflates can be used instead of chloride 8.

In addition to the methods described above, compounds of this invention can also be prepared as described in scheme 5 below.

Scheme 5

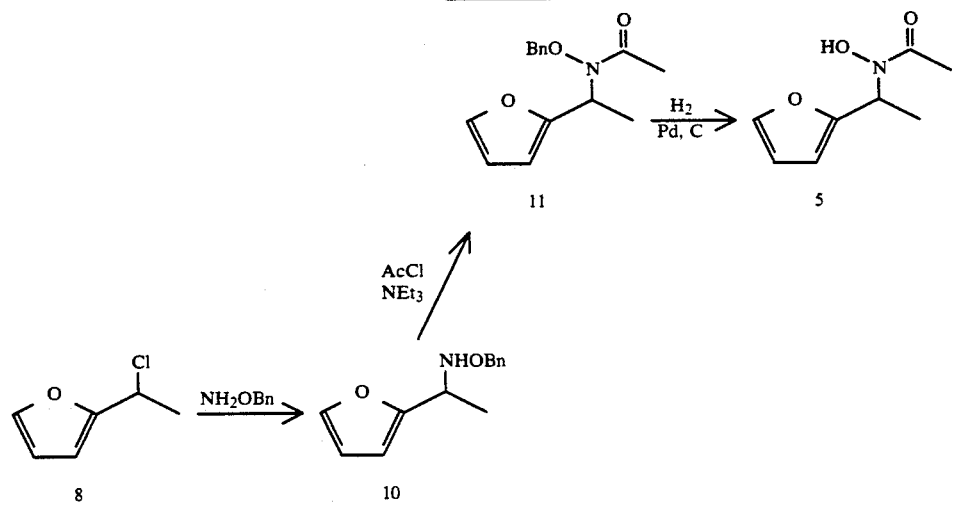

Scheme 5
-continued

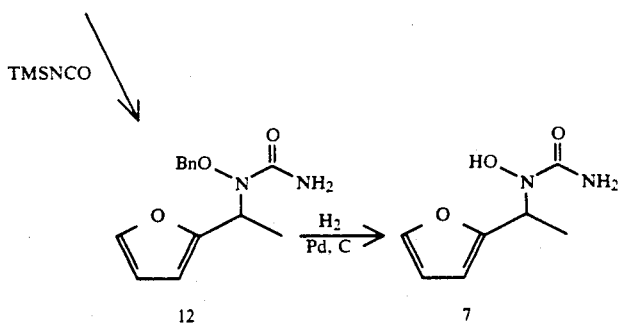

Chloride 8 is heated with O-benzylhydroxylamine in a solvent such as dimethylsulfoxide or tetrahydrofuran to yield the new hydroxylamine 10. This can either be reacted with acetyl chloride as in scheme 1 to yield 11 or with trimethylsilyl isocyanate as in scheme 3 to yield 12. Compounds 11 and 10 are then hydrogenated to yield 5 and 7, respectively. Other O-protected hydroxylamines can also be used in place of O-benzylhydroxylamine such as O- tetrahydropyranyl hydroxylamine. Further, other methods can be used to convert 10 to 7, such as treatment with phosgene followed by ammonium hydroxide such as described in scheme 2, or treatment with sodium cyanate as described in scheme 3.

Compounds of this invention in which A is —CH$_2$— or —CH(alkyl)— can also be prepared as described in scheme 6.

Scheme 6

Furan 13 is first converted to 2-lithiofuran by treatment with n-butyllithium. This is then treated with the O- benzyloxime of acetaldehyde in the presence of BF$_3$.Et$_2$O to give O-benzylhydroxylamine 10. This can be converted to the compounds such as 5 or 7 as described in scheme 4. Other O- protected oximes can be substituted for the O-benzyl oxime and other Lewis acids such as CeCl$_3$ can be used. The following examples further illustrate the synthesis and use of compounds of this invention. The appropriate designations for R$_1$, A, X and Y as defined by formula I are given for each example below.

Example 1

N-hydroxy-N-(1-(5-methylfur-2-yl)ethyl) urea a. 2-Acetyl-5-methylfuran oxime. 2-Acetyl 5-methylfuran (5 g, 40.3 mmole) and hydroxylamine hydrochloride (4.2 g, 60.4 mmole) were dissolved in a mixture of ethanol (20mL) and pyridine (6.5 mL) and heated at 50° C. for 2 hours. The reaction mixture was diluted with water (300 mL) and extracted twice with ethyl acetate. The organic layer was washed with 2N HCl and brine, dried over MgSO$_4$ and concentrated in vacuo to provided 4.31 g of the desired product.

b. 1-(5-Methylfur-2-yl)ethyl hydroxylamine. The oxime prepared as in step b above (4.2q, 30 mmole) was dissolved in ethanol (200 mL) and cooled to 0° C. Borane pyridine complex (10 mL, 100 mmole) was added via syringe under nitrogen followed one hour later by 6N HCl (100 mL). Within thirty minutes the reaction was complete and was brought to pH 9 with the addition of 2N NaOH. The mixture was extracted into ethyl acetate and dried over MgSO$_4$. After evaporation, the residue was chromatographed on 150 g silica gel, eluting with 60% ether in hexanes to obtained 1.8 g of a clear liquid.

c. N-Hydroxy-N-(1-(5-methylfur-2-yl)ethyl) urea. Using the method of scheme 3, 1-(5-methylfur-2-yl)ethyl hydroxylamine prepared as described above in step b (1.8 g, 14.4 mmole), was refluxed for thirty minutes with trimethylsilyl isocyanate (3.3 g, 28.8 mmole) in dioxane (40 mL). The reaction mixture was then washed with saturated NH$_4$Cl solution. The organic layer was dried with MgSO$_4$, and evaporated. The residue was chromatographed on 75 g silica gel eluting with ethyl acetate to provide the desired product. (R1=—NH$_2$, A=2—(—CH(CH$_3$)—), X=O, Y=5-methyl)

Melting Point: 116°–118° C.

NMR (300 MHz, DMSO-d6): 1.32 (d, 3H, J=7.5 Hz); 2.21 (s, 3H); 5.25 (q, 1H, J=7.5); 5.95 (m, 1H); 6.08 (m, 1H); 6.36 (br s, 2H); 8.90 (s, 1H).

IR (KBr): 3450, 3360, 3320, 2880, 1640, 1480.

Mass spectrum (CI-NH$_3$): 185 (M+1)$^+$, 202 (M+NH$_4$)$^+$.

Analysis (C$_8$H$_{12}$N$_2$O$_3$): Calculated—C: 52.17, H: 6.57, N: 15.21; Found C: 52.11, H: 6.61, N: 15.12.

Example 2

N-hydroxy-N-(1-(5-phenylfur-2-yl)ethyl) urea a. 2-Phenyl furan. n Butyl lithium (60 mL, 2.5M in hexane) was added to a solution of furan (10.2 g, 1.5 mmole) in THF (100 mL). The mixture was stirred for 3 hours at 0° C. and transferred via cannula to a stirred suspension of zinc chloride (20.1 g, 150 mmole) in THF (100 mL). The mixture was stirred one hour and then a solution of tetrakis(triphenylphosphine) palladium 0.57 g, 0.5 mmole) in tetrahydrofuran was added at room temperature. Bromobenzene (15.7 g, 100 mmol) was then added and the temperature increased to 50° C. for 24 hours. 0.1N HCL (100 mL) was added to the cooled solution followed by ether (100 mL) The organic phase was washed with saturated sodium carbonate and brine, dried with MgSO$_4$ and evaporated. The residue was distilled (50°–55° C./0.6–0.9 torr) to give 12 g of the desired product.

b. 2-Acetyl-5-phenyl furan. n-Butyl lithium (33.6 mL, 2.5M in hexanes) was added dropwise to a solution of 2-phenylfuran, prepared as described in step a, above, (12 g, 83.2 mmole). After being stirred for 30 minutes N,O- dimethylacetohydroxamic acid was added and allowed to stir at −20° C. for 1 hour, then at room temperature for 2 hours. The reaction was quenched with the addition of saturated ammonium chloride solution. The mixture was extracted with ether and the organic layer was washed with brine and dried over MgSO$_4$. The solvent was removed in vacuo to yield 15.2 g of the desired product.

c. N-Hydroxy-N-(1-(5-phenylfur-2-yl)ethyl) urea was prepared according to the method of example 1, except using 2-acetyl 5-phenyl furan instead of 2-acetyl-5-methyl furan. (R1=—NH$_2$, A=2—(—CH(CH$_3$)—), X=O, Y=5-phenyl).

Melting Point: 133°–136° C.
NMR (300 MHz, DMSO-d6): 1.41 (d, 3H, J=6.9Hz); 5.38 (q, 1H, J=6.9 Hz); 6.35 (dd, 1H, J=1,3.3Hz); 6.48 (s, 2H); 6.85 (d, 1H); 7.22–7.45 (m, 3H); 7.62–7.68 (m, 2H); 9.11 (s, 1H).
IR (CDCl$_3$): 3450, 3440, 1570, 1425, 1650.
Mass spectrum (CI-NH$_3$): 247 (M+1)$^+$, 264 (M+NH$_4$)$^+$, 171.
Analysis (C$_{13}$H$_{14}$N$_2$O$_3$): Calculated—C: 63.40, H: 5.73, N: 11.38; Found C: 62.82, H: 5.79, N: 11.22.

Example 3

N-hydroxy-N-(1-(5-phenylfur-2-yl)ethyl)-N'-methyl urea

The desired material was prepared according to the method of example 2, except using methyl isocyanate instead of trimethylsilyl isocyanate. (R1=—NHCH$_3$, A=2—(—CH(CH$_3$)—), X=O, Y=5-phenyl).

Melting Point: 120°–123° C.
NMR (300 MHz, DMSO-d6): 1.41 (d, 3H, J =6.6 Hz); 2.66 (d, 3H, J=3.9 Hz); 5.35 (q, 1H, J =6.6 Hz); 6.33 (dd, 1H, J=1, 3.3 Hz); 6.84 (d, 1H, J=3.3 Hz); 7.01 (q, 1H); 7.27 (m, 1H); 7.37–7.45 (m, 2H); 7.6–7.65 (m, 2H); 9.03 (s, 1H).
IR (CDCl$_3$): 3535, 3455, 1660, 1530.
Mass spectrum (CI-NH$_3$): 261 (M+1)$^+$, 278 (M+NH$_4$)$^+$, 171.
Analysis (C$_{14}$H$_{16}$N$_2$O$_3$): Calculated—C: 64.60, H: 6.20, N: 10.76; Found C: 64.18, H: 6.19, N: 10.80.

Example 4

N-hydroxy-N-(1-(5-phenylfur-2-yl)ethyl) acetamide a. N-Acetoxy-N-(1-(5-phenylfur-2-yl)ethyl) acetamide. 1-(5-Phenylfur-2-yl)ethyl hydroxylamine (2.75 g, 13.5mmole) prepared as in example 1 above and triethyl amine (4.7 g, 33.7 mmole) were dissolved in CH$_2$Cl$_2$ and acetyl chloride (2.2 mL, 29.7 mmole) was added. The mixture was stirred for thirty minutes and poured into 2N HCl. The organic layer was dried over CH$_2$Cl$_2$ and evaporated. The residue was carried on without purification.

b. N-Hydroxy-N-(1-(5-phenylfur-2-yl)ethyl) acetamide. The material prepared as described in step a above (3.8 g, 13.5 mmole) was dissolved in isopropanol (50 mL) and added to a solution of lithium hydroxide (2.26 g, 54 mmole) in water (25 mL). The mixture was stirred for 1 hour and then partitioned between 1N HCl and ether. The organic phase was dried over MgSO$_4$ and concentrated in vacuo. The residue was recrystallized from ether to give 2.026 g of the desired material. (R1=—CH$_3$, A=2—(—CH(CH$_3$)—), X=O, Y=5-phenyl).

Melting Point: 136° C.
NMR (300 MHz, DMSO-d6): 1.46 (d, 3H, J=6.6 Hz); 2.05 (s, 3H); 5.71 (q, 1H, J=6.6 Hz); 6.42 (dd, 1H, J=1Hz, 3.3 Hz); 6.87 (d, 1H,); 7.27 (m, 1H); 7.37–7.46 (m, 2H); 7.61–7.68 (m, 2H); 9.58 (s, 1H).
IR (CDCl$_3$): 2940, 2990, 1482, 1442, 1620.
Mass spectrum (CI-NH$_3$): 246 (M+1)$^+$, 263 (M+NH$_4$)$^+$, 171.
Analysis (C$_{14}$H$_{15}$NO$_3$): Calculated—C: 68.56, H: 6.16, N: 5.71; Found C: 67.61, H: 6.29, N: 5.61.

Example 5

N-hydroxy-N-(1-(5-(2-phenylethenyl)fur-2-yl)ethyl) urea a. 2-(2-Phenylethenyl) furan. n-Butyl lithium (16 mL, 2.5M in hexanes) was added to a solution of diethyl benzylphosphonate (9.2 g, 40.3 mmole) at −78° C. After being stirred for 15 min furfural (3.4 mL, 40.3 mmole) was added. The reaction was stirred for an additional 15 minutes at −78° C. and then at room temperature for 5 hours. Ammonium chloride solution was added to quench the reaction and the mixture was partitioned between ether and water. The organic layer was dried over MgSO$_4$ and concentrated. The residue was chromatographed on 500 g silica gel eluting with CH$_2$Cl$_2$/pentane (1:10). A yield of 2.8 g of the desired material was obtained.

b. N-Hydroxy-N-(1-(5-(2-phenylethenyl)fur-2-yl)ethyl) urea. The desired compound was prepared using the method of example 2, except using the 2-(2-phenylethenyl) furan instead of 2 phenylfuran. (R1=—NH$_2$, A=2—(—CH(CH$_3$)—), X=O, Y=-5—(C$_6$H$_5$CH=CH—).

Melting Point: 140°–143° C.
NMR (300 MHz, DMSO-d6): 1.60 (d, 3H, J =7.2 Hz); 5.35 (q, 1H, 7.2 Hz); 6.32 (dd, 1H, J=1, 3.3 Hz); 6.46 (d, 1H; 3.3 Hz); 6.49 (s, 2H); 6.90 (d, 1H, J=16.5 Hz); 7.07 (d, 1H, J =16.5 Hz); 7.2–7.4 (m, 3H); 7.5–7.6 (m, 2H); 9.11 (s, 1H).
IR (CDCl$_3$): 3470, 1655, 1575, 1445.
Mass spectrum (CI-NH$_3$): 273 (M+1)$^+$, 290 (M+NH$_4$)$^+$, 197.
Analysis (C$_{15}$H$_{16}$N$_2$O$_3$): Calculated—C: 66.16, H: 5.92, N: 10.92; Found C: 64.90, H: 6.08, N: 9.68.

Example 6

N-hydroxy-N-(1-(5-(2-phenylethenyl)fur-2-yl)ethyl)-N'-methyl urea

The desired compound was prepared according to the method of example 5, except using methyl isocyanate instead of trimethylsilyl- isocyanate. (R1=—NHCH$_3$, A=2—(—CH(CH$_3$)—), X=O, Y=-5—(C$_6$H$_5$CH=CH—).

Melting Point: 156°–159° C.
NMR (300 MHz, DMSO-d6): 1.49 (d, 3H, J =6.9 Hz); 2.66 (d, 3H, J =3.6 Hz); 5.82 (q, 1H, 6.9 Hz); 6.30 (dd, 1H, J =1, 3.3 Hz); 6.45 (d, H, J =3.3 Hz); 6.87 (d, 1H, J=16.5 Hz); 7.0–7.01 (m, 2H); 7.2–7.4 (m, 3H); 7.5–7.6 (m, 2H); 9.04 (s, 1H).
IR (CDCl$_3$): 3450, 1665, 1530.
Mass spectrum (CI-NH$_3$): 287 (M+1)$^+$, 304 (M+NH$_4$)$^+$, 197.
Analysis (C$_{16}$H$_{18}$N$_2$O$_3$): Calculated—C: 67.12, H: 6.34, N: 9.78; Found C: 66.81, H: 6.50, N: 9.67.

Example 7

N-hydroxy-N-(1-fur-2-ylethyl) propionamide

The desired compound was prepared according to the method of example 4, except using 2-acetyl furan instead of 5- phenyl-2-acetyl furan. (R1=CH$_3$CH$_2$—, A=2—(—CH(CH$_3$)—), X=O, Y=H).

Melting Point: 74°-76° C.

NMR (300 MHz, DMSO-d6): 0.99 (t, 3H); 1.40 (d, 3H); 2.38 (q, 2H); 5.65 (q, 1H); 6.28 (m, 1H); 6.39 (m, 1H); 7.52 (m, 1H); 9.42 (br s, 1H).

Mass spectrum (CI-NH$_3$): 183 M+, 166, 110, 95.

Example 8

N-hydroxy-N-(1-(1-methyl-5-phenylpyrrol-2-yl)ethyl) N'- methyl urea a. 1-Methyl-2-phenyl pyrrole was prepared according to the method of example 2, step a, except using 1-methylpyrrole instead of furan b. N-Benzyloxy-1-(1-methyl-5-phenylpyrrol-2-yl)ethylamine. t-Butyl lithium (4.1 ml, 1.7M in hexanes) was added to a solution of the pyrrole prepared as in step a, above (1.0 g, 6.4 mmole) in THF (25 mL) at −78° C. After stirring for 30 minutes, boron trifluoride etherate (0.99 g, 7.0 mmole) was added followed by O-benzyl acetaldehyde oxime (1.0 g, 7.0 mmole). The mixture was stirred for 15 min, saturated NH$_4$Cl solution was added, and the mixture was allowed to warm to room temperature. The aqueous phase was washed twice with brine, dried over MgSO$_4$ and concentrated. The residue was chromatographed on 100 g of silica gel eluting with 20% ether in hexanes to give 0.34 g of the desired product.

c. N-benzyloxy-N-(1-(1-methyl-5-phenylpyrrol-2-yl)ethyl) N'-methyl urea was prepared using the method of example 1, step c, except using the material prepared as in part b, above instead of 1-(5-methylfur-2-yl)ethyl hydroxylamine, and using methyl isocyanate instead of trimethylsilyl isocyanate.

d. N-hydroxy-N-(1-(1-methyl-5-phenylpyrrol-2-yl)ethyl) N'-methyl urea. The material prepared as in part c, above was dissolved in methanol and palladium oxide on carbon (25 mg) added. The reaction mixture was stirred under a positive atmosphere of hydrogen overnight. The mixture was concentrated and the residue azeotroped with benzene to give the desired product as a tan powder. (R1=—NH$_2$, A=2—(—CH(CH$_3$)—), X=NCH$_3$, Y=5-phenyl).

Melting Point: 158°-161° C.

NMR (300 MHz, DMSO-d6): 1.35 (d, 3H, J=7.5 Hz); 2.62 (d, 3 H, J=4.5 Hz); 3.44 (s, 3H); 5.41 (m, 1H); 6.07 m, 2H); 6.87 (m, 1H); 7.30 (m, 1H); 7.41 (m, 4H).

Mass spectrum (CI-NH$_3$): 274 (M+1)+, 258, 184, 158.

Example 9

N-hydroxy-N-(3-fur-2-ylprop-2-enyl) urea

The desired material was prepared according to the method of example 1, except using 3-fur-2-ylpropenal instead of 2-acetyl-5-methylfuran. (R1=—NH$_2$, A=-2—(—CH=CHCH$_2$—), X=O, Y=H).

Melting Point: 118°-121° C.

NMR (300 MHz, DMSO-d6): 4.06 (m, 2H); 6.06 (dt, 1H, J=16.5, 6 Hz); 6.41 (m, 4H); 6.47 (m, 1H); 7.60 (m, 1H); 9.33 (s, 1H).

Mass spectrum (CI-NH$_3$): 183 (M+1)+, 200 (M+NH$_4$)+, 167, 107.

Analysis (C$_8$H$_{10}$N$_2$O$_3$): Calculated—C: 52.74, H: 5.53, N: 15.38; Found C: 52.51, H: 5.59, N: 1520.

Example 10

N-hydroxy-N-fur-3-ylmethyl urea

The desired compound was prepared according to the method of example 1, except using 3-furancarboxaldehyde instead of 2-acetyl-5-methyl furan. (R=—NH$_2$, A=3—(—CH$_2$—), X=O, Y=H).

Melting Point: 125°-128° C.

NMR (300 MHz, DMSO-d6): 4.31 (s, 2H); 6.34 (brs, 2H); 6.40 (m, 1H); 7.56 (m, 2H); 9.30 (s, 1H).

Mass spectrum (CI-NH$_3$): 157 (M+1)+, 174 (M+NH$_4$)+,

Analysis (C$_6$H$_8$N$_2$O$_3$): Calculated—C: 46.15, H: 5.16, N: 17.94; Found C: 45.80, H: 5.09, N: 17.72.

Example 11

N-hydroxy-N-fur-3 ylmethyl-N'-methyl urea

The desired compound was prepared according to the method of example 1, except using 3-furancarboxaldehyde instead of 2- acetyl-5-methyl furan and using methyl isocyanate instead of trimethylsilyl isocyanate. (R1=—NHCH$_3$, A=3—(—CH$_2$—), X=O, Y=H).

Melting Point: 129°-131° C.

NMR (300 MHz, DMSO-d6): 2.58 (d, 3H, J=7.5 Hz); 4.30 (s, 2H); 6.39 (brs, 2H); 6.90 (m, 1H); 7.55 (m, 2H); 9.22 (s, 1H).

Mass spectrum (CI-NH$_3$): 171 (M+1)+, 188 (M+NH$_4$)+,

Analysis (C$_7$H$_9$N$_2$O$_3$): Calculated—C: 49.41, H: 5.92, N: 16.46; Found C: 49.14, H: 5.97, N: 16.49.

Example 12

N-hydroxy-N-(5-(2,4,6-trimethylphenyl)-fur-2-ylethyl) urea

The desired compound was prepared according to the method of example 2, except using mesityl bromide instead of bromobenzene and using methyl isocyanate instead of trimethylsilyl isocyanate. (R1=—NH$_2$, A=-2—(—CH(CH$_3$)—), X=O, Y=5—(2,4,6-trimethylphenyl)).

Melting Point: 139°-141° C.

NMR (300 MHz, DMSO-d6): 1.40 (d, 3H, J=6.9 Hz); 2.13 (s, 6H); 2.25 (s, 3H); 5.35 (q, 1H, 6.9 Hz); 6.28-6.32 (m, 2H); 6.39 (s, 2H); 6.91 (s, 2H); 9.07 (s, 1H).

IR (CDCl$_3$): 3530, 2360, 2340, 1670, 1560.

Mass spectrum (CI-NH$_3$): 289 (M+1)+, 306 (M+NH$_4$)+, 213.

Analysis (C$_{16}$H$_{20}$N$_2$O$_3$): Calculated—C: 66.65, H: 6.99, N: 9.72; Found C: 6.64, H: 7.08, N: 9.72.

Example 13

N-hydroxy-N-(1-(5-butylfur-2-ylethyl) urea

The desired compound was prepared according to the method of example 2, steps b and c except using 2-butyl furan instead of 2-phenylfuran. (R1=—NH$_2$, A=2—(—CH(CH$_3$)—), X=O, Y=5-butyl).

Melting Point: 105°-107.5° C.

NMR (300 MHz, DMSO-d6): 0.89 (t, 3H); 1.32 (m, 5H); 1.53 (m, 2H); 5.74 (m, 1H); 5.95 (m, 1H); 6.08 (m, 1H); 6.36 (br s, 2H); 8.97 (s, 1H).

Mass spectrum (CI-NH$_3$): 227 (M+1)+, 244(M+NH$_4$)+, 151.

Examples 14–31 are prepared in a manner generally analogous to those described in examples 1–13 and schemes 1–6.

Example 14

N-hydroxy-N-(1-(5-phenylmethylfur-2-yl)ethyl) urea (R1=—NH$_2$, A=2—(—CH(CH$_3$)—), X=O, Y=5-benzyl)

Example 15

N-hydroxy-N-(1-(5-ethylfur-2-yl)ethyl) methylpropionamide (R1=—CH(CH$_3$)$_2$, A=2—(—CH(CH$_3$)—), X=O, Y=5-ethyl)

Example 16

N-hydroxy-N-(1-(3,4-dimethylfur-2-yl)ethyl) propenamide (R1=CH=CH$_2$, A=2—(—CH(CH$_3$)—), X=O, Y=3,4-dimethyl)

Example 17

N-hydroxy-N-(1-(3-methylfur-2-yl)ethyl)-N',N'-dimethylurea (R1=—N(CH$_3$)$_2$, A=2—(—CH(CH$_3$)—), X=O, Y=3-methyl)

Example 18

N,N'-dihydroxy-N-(1-(5-methylfur-2-yl)ethyl) urea (R1=—NHOH, A=2—(—CH(CH$_3$)—), X=O, Y=5-methyl)

Example 19

N-hydroxy-N-(2-fur-2-ylethyl) urea (R1=—NH$_2$, A=2—(—CH$_2$CH$_2$—), X=O, Y=H)

Example 20

N-hydroxy-N-(1-methyl-1-fur-2-ylethyl) urea (R1=—NH$_2$, A=2—(—CH$_2$CH(CH$_3$)—), X=O, Y=H)

Example 21

N-hydroxy-N-pyrrol-2-ylmethyl urea (R1=—NHCH$_3$, A=2—(—CH$_2$—), X=NH, Y=H)

Example 22

N-hydroxy-N-(pyrrol-2-ylmethyl) urea (R1=—NH$_2$, A=—CH$_2$—, X=NH, Y=H

Example 23

N-hydroxy-N-(5-fluoro-(1-fur-2-yl)ethyl) urea (R1=—NH$_2$, A=2—(—CH(CH$_3$)—), X=O, Y=5-fluoro)

Example 24

N-hydroxy-N-(3-trifluoromethyl-(1-fur-2-yl)ethyl) urea (R1=—NH$_2$, A=2—(—CH(CH$_3$)—), X=O, Y=3-trifluoromethyl)

Example 25

N-hydroxy-N-(5-phenylmethoxy-(1 fur-2-yl)ethyl) urea (R1=—NH$_2$, A=2—(—CH(CH$_3$)—), X=O, Y=5-benzyloxy)

Example 26

N-hydroxy-N-(4-benzoyl-(1-fur-2-yl)ethyl) urea (R1=—NH$_2$, A=2—(—CH(CH$_3$)—), X=O, Y=4-benzoyl)

Example 27

N-hydroxy-N-(1-acetoxy-(1-pyrrol-2-yl)ethyl) urea (R1=—NH$_2$, A=2—(—CH(CH$_3$)—), X=NCOCH$_3$, Y=H)

Example 28

N-hydroxy-N-(1-benzoyl-(1-pyrrol-2-yl)ethyl) urea (R1=—NH$_2$, A=2—(—CH(CH$_3$)—), X=NCOC$_6$H$_5$, Y=H)

Example 29

N-hydroxy-N-(1-(5-(4-fluorophenyl)-1-fur-2-yl)ethyl) urea (R1=—NH$_2$, A=2—(—CH(CH$_3$)—), X=O, Y=5-(4-fluorophenyl))

Example 30

N-hydroxy-N-(1-(5-(3,5-dimethoxyphenylmethylfur-2-yl)ethyl) urea (R1=—NH$_2$, A=2—(—CH(CH$_3$)—), X=O, Y=5-(3,5-dimethoxyphenylmethyl))

Example 31

N-hydroxy-N-(1-(3-hydroxyfur-2-yl)ethyl) urea (R1=—NH$_2$, A=2—(—CH(CH$_3$)—), X=O, Y=3-hydroxy)

Example 32

N-hydroxy-N-(1-(5-methylfur-2-yl)ethyl) urea sodium salt

The material prepared as in example 1 is dissolved in tetrahydrofuran and one equivalent of sodium hydride is added. After hydrogen evolution ceases, hexane is added and the desired product collected by filtration. (R1=—NH$_2$, A=2—(—CH(CH$_3$)—), X=O, Y=5-methyl, M=Na).

Example 33

N-hydroxy-N-(1-(5-methylfur-2-yl)ethyl) urea ammonium salt

The material prepared as in example 1 is dissolved in tetrahydrofuran and ammonia is bubbled through the solution. Hexane is added and the desired product collected by filtration. (R1=NH$_2$, A=2—(—CH(CH$_3$)—), X=O, Y=5-methyl, M=NH$_4$).

Example 34

N-hydroxy-N-(1-(5-methylfur-2-yl)ethyl) urea tetrabutylammonium salt

The material prepared as in example 1 is dissolved in tetrahydrofuran and one equivalent of tetrabutyl ammonium hydroxide is added. Hexane is added and the desired product collected by filtration. (R1=—NH$_2$, A=2—(—CH(CH$_3$)—), X=O, Y=5-methyl, M=N(C$_4$H$_9$)$_4$.

Example 35

N-butyroxy-N-(1-(5-methylfur-2-yl)ethyl) urea

The material prepared as in example 1 and 1.1 equivalents of triethylamine are dissolved in tetrahydrofuran and 1 equivalent of butyryl chloride is added. Ether is added and the material is washed with 2N HCl, dried with MgSO$_4$ and then evaporated to yield the desired product. (R1=—NH$_2$, A=2—(—CH(CH$_3$)—), X=O, Y=5-methyl, M=COC$_3$H$_7$).

Example 36

N-hydroxy-N-(1-fur-2-ylethyl) urea a) To a solution of acetyl furan (25 g, 0.23 mol) in EtOH (40 mL) was added pyridine (37 mL, 0.45 mol) and hydroxylamine hydrochloride (24 g, 0.34 mol) with stirring. The flask was heated to 50° C. for 1.5 hours then cooled to room temperature and diluted with 50 mL water and 30 mL ethyl acetate. The aqueous layer was extracted with ethyl acetate (3×, 20 mL). The combined organic extract was washed with 2M HCl (1×, 20 mL), brine (1×, 20 mL), dried over anhydrous MgSO$_4$, filtered and evaporated to give the oxime intermediate (29 g).

b) The oxime (14 q, 0.11 mol) from the previous step was dissolved in EtOH (200 mL) and treated with borane-pyridine (34 mL, 0.34 mol). The solution was stirred 30 min at room temperature and then the flask was cooled to 0° C. and 6N HCl (366 mL) was added slowly. When the heat of the reaction had subsided the flask was warmed to room temperature and stirred until the reaction was complete. The solution was diluted with water (100 mL) and the pH adjusted to 8-9 by the addition of solid sodium carbonate. The aqueous solution was extracted with ethyl acetate (3×100 mL) and the combined organic extract was washed with brine (1×150), dried over MgSO$_4$, filtered and concentrated to give an oil. Chromatography (silica gel, 60% ether in hexanes) gave the desired hydroxylamine intermediate (8.5 g).

c) To a solution of trimethylsilylisocyanate (14 mL, 0.09 mol) in 100 mL tetrahydrofuran (THF) was added the oxime from part b) (5.5 g, 0.04 mol) in 25 mL THF. The reaction was warmed to reflux, stirred for 1 h, cooled to room temperature and diluted with saturated ammonium chloride solution (50 mL). The aqueous layer was extracted with ethyl acetate (3×100 mL). The organic extract was with brine (100 mL), dried over MgSO$_4$, filtered and evaporated. The crude material was triturated with ether and filtered. Recrystallization from ethyl acetate yielded the desired product (4.2 g); m.p.=143°-144° C.; $^1$H NMR(300 MHz, DMSO-d6) 9.04 (bs, 1H), 7.53 (m, 1H), 6.37 (m, 3H), 6.22 (m, 1H), 5.31 (q, J=5.40, 13.51 Hz, 1H), 1.33 (d, J=7.21 Hz, 3H); MS: (M+H)$^+$ at 171; Analysis Calc'd for C$_7$H$_{10}$N$_2$O$_3$: C, 49.39; H, 5.93; N, 16.47. Found: C, 49.50; H, 6.04; N, 16.52.

Example 37

N-hydroxy-N-(5-methylfur-2-ylmethyl) urea

The desired material was prepared according to the method of Example 36, except using 5-methyl-2-furancarboxaldehyde instead of acetyl furan. The desired product was recrystallized from ethyl acetate and hexanes; mp=105° C.; $^1$H NMR (300 MHz, DMSO-d6): 9.33 (bs, 1H), 6.37 (bs, 2H), 6.13 (d, J =3.02 Hz, 1H), 5.98 (m, 1H), 4.39 (bs, 2H), 2.21 (s, 3H); MS (M+H)$^+$=171.

Example 38

N-hydroxy-N-(5-methylfur-2-yl)methyl-N'-methyl urea

The desired material was prepared according to the method of Example 36, except using 5-methyl-2-furancarboxaldehyde instead of acetylfuran and methylisocyanate instead of trimethylsilyl-isocyanate.

Example 39

N-hydroxy-N-(1-(5-methylfur-2-yl)ethyl)-N'-phenyl urea

To a solution of phenyl isocyanate (0.87 mL, 8.0 mmol) in 10 mL THF was added N-(1-(5-methyl-fur-2-yl)ethyl) hydroxylamine (0.50 g, 4.0 mmol) in 3 mL THF. The reaction was stirred 1 h at room temperature and was quenched with saturated ammonium chloride solution (25 mL). The aqueous layer was extracted with ethyl acetate (3×10 mL) and the organic layer was washed with brine (1×20 mL). The solution was dried with MgSO$_4$, filtered and evaporated. Chromatography (silica gel, 30% ether/hexanes) gave 0.32 g of desired product; m.p.=109°-110° C.; $^1$H NMR (300 MHz, DMSO-d6) 9.43 (bs, 1H), 8.97 (bs, 1H), 7.62 (dd, J=1.50, 8.71 Hz, 2H), 7.25 (m, 2H), 6.96 (m, 1H), 6.15 (d, J=3.00 Hz, 1H), 5.38 (q, J=6.9, 17.4 Hz, 1H), 2.19 (s, 3H), 1.39 (d, J=6.30 Hz, 3H); MS (M+H)$^+$=261; Analysis calc'd for C$_{14}$H$_{16}$N$_2$O$_3$: C, 64.59; H, 6.20; N, 10.77. Found: C, 64.00; H, 6.12; N, 10.60.

Example 40

N-hydroxy-N-(1-(5-methylfur-2-yl)ethyl)-N'-(4-carboethoxyphenyl) urea

The desired material was prepared according to the method of Example 39, except using ethyl 4-isocyanatobenzoate instead of phenyl isocyanate. The product was chromatographed over silica gel with 60% ether/hexanes to yield a sticky white gum. $^1$H NMR (300 MHz, DMSO-d6) 9.57 (bs, 1H), 9.37 (bs, 1H), 7.83 (m, 4H), 6.16 (d, J=2.85 Hz, 1H), 5.98 (m, 1H), 5.40 (q, J=6.60, 14.41 Hz, 1H), 4.27 (q, J=6.60, 13.51 Hz, 2H), 2.09 (s, 3H), 1.42 (d, J=6.60 Hz, 3H), 1.30 (t, J=6.33 Hz, 3H); MS (M+H)$^+$=333.

Example 41

N-hydroxy-N-(1-(5-methylfur-2-yl)ethyl)-N'-(4-carboxamidophenyl) urea

To a solution of ammonium chloride (0.70 g, 13 mmol) in 75 mL of dry methylene chloride at −78° C. was added trimethylaluminum (13 mL, 26 mmol; 2M solution in hexanes) via syringe. The solution was stirred 15 min at −78° C. and was warmed to −20° C. for 30 min and then room temperature for 1 h. The solution was cooled to 0° C. and N-hydroxy-N-(1-(5-methyl-fur-2yl)ethyl) N'-(4- carboethoxyphenyl) urea (1.4 g, 4.3 mmol) in 20 mL of methylene chloride was slowly added. The solution was warmed to room temperature and then refluxed for 24 h. When the mixture cooled to room temperature, 2.2 mL of 2M HCl was very slowly added and the solution was stirred 30 min, filtered and the solid was collected. The solid was placed in 30 mL of 10% HCl solution and allowed to stir for 48 h and then filtered. The solid was then recrystallized from ethanol/hexanes to yield 205 mg of product; m.p.=170°-171° C.; $^1$H NMR (300 MHz, DMSO-d6) 9.53 (bs, 1H), 9.22 (bs, 1H), 7.82 (bs, 1H), 7.77 (m, 4H), 7.19 (bs, 1H), 6.16 (d, J=3.30 Hz, 1H), 5.97 (m, 1H), 5.40 (q, J=6.90, 13.81 Hz, 1H), 2.20 (s, 3H), 1.41 (d, J=6.60 Hz, 3H); MS (M+H)+ =304; Analysis calc'd for $C_{15}H_{17}N_3O_4$: C, 59.38; H, 5.65; N, 13.86. Found: C, 58.88; H, 5.40; N, 13.53.

Example 42

N-hydroxy-N-(1-(5-methylfur-2-yl)ethyl)-4-methylsulfonyl benzamide

To a solution of 4-(methylsulfonyl) benzoic acid (3.1 g, 15.5 mmol) in 100 mL of methylene chloride was added dimethylformamide (1.2 mL, 15.5 mmol). The reaction vessel was cooled to 0° C. and oxalyl chloride (3.1 mL, 35 mmol) was added. The mixture stirred 1 h at 0° C. and was added to a solution of N-(1-(5-methylfur-2-yl)ethyl) hydroxylamine (2.6 g, 18.6 mmol) and triethylamine (3.3 mL, 23.3 mmol) in 75 mL methylene chloride at 0° C. The mixture stirred 1.5 h and was poured into 2M HCl (100 mL). The aqueous layer was extracted with methylene chloride (3×, 100 mL) and the combined organic extract was washed with saturated sodium bicarbonate solution (1×100 mL) and brine (1×100 mL). The solution was dried over MgSO4, filtered and evaporated. The material was recrystallized from ethyl acetate to yield 1.14 g of a white solid; m.p.=177° C.; 1H NMR (300 MHz, DMSO-d6) 9.85 (bs, 1H), 7.97 (d, J=8.41 Hz, 2H), 7.83 (d, J=9.01 Hz, 2H), 6.24 (d, J=3.60 Hz, 1H), 6.02 (m, 1H), 5.71 (bs, 1H), 3.26 (s, 3H), 2.24 (s, 3H), 1.47 (d, J=6.91 Hz, 3H). MS (M+H)+ =324; Analysis calc'd for $C_{15}H_{17}NO_5$: C, 55.20; H, 5.25; N, 4.29. Found: C, 55.07; H, 5.20; N, 4.23.

Example 43

N-hydroxy-N-(1-(5-carbomethoxyfur-2-yl)ethyl urea a) To a solution of diisopropylamine (27.5 mL, 0.20 mol) in 200 mL of THF at 0° C. was added n-butyllithium (78.5 mL, 0.196 mol; 2.5M in hexanes). The solution was stirred 30 min and was cooled to −78° C. A solution of furoic acid (10.0 g, 0.089 mol) in 100 mL of THF was added and the solution stirred 30 min. To this mixture was added N-methoxy- N-methyl-acetamide (13.8 g, 0.134 mol) in 50 mL of THF. The reaction mixture was warmed to room temperature and stirred 1 h. The mixture was quenched with saturated ammonium chloride solution and the aqueous layer was washed with ether (3×50 mL) to remove impurities. The aqueous layer was acidified with 2M HCl and extracted with ethyl acetate (3×100 mL). The combined organic extract was washed with brine, dried over MgSO4, filtered and evaporated to yield 11.1 g (81%) of 2-acetyl-fur-5-yl carboxylic acid.

b) A solution of 2-acetyl-fur-5-yl carboxylic acid (1.0 g, 6.49 mmol) was dissolved in 25 mL of methanol. HCl(g) was bubbled through the solution until it was saturated. The methanol solution was then warmed to 60° C. and allowed to stir 45 min. The solution was concentrated to 5 mL and then diluted with ether. The ether layer was washed with saturated sodium bicarbonate solution and dried over MgSO4, filtered and evaporated to yield 880 mg (81%) of 5-acetyl-2-methoxycarbonylfuran.

c) To a solution cf 2-acetyl-5-methoxy-carbonylfuran (0.88 g, 5.24 mmol) in 2.5 mL ethanol at room temperature was added pyridine (0.85 mL, 10.5 mmol) and hydroxylamine hydrochloride (0.55 g, 7.86 mmol) with stirring. The reaction was complete after 1 h at room temperature. The solution was diluted with water and extracted with ethyl acetate (3×25 mL). The combined organic extract was washed with 2M HCl (30 mL), and brine (30 mL) and dried over MgSO4, filtered and concentrated to yield 1.09 g of the corresponding oxime intermediate.

d) The oxime of 2-acetyl-5-methoxycarbonylfuran (1.09 g, 5.95 mmol) was dissolved in 5 mL ethanol at room temperature and borane-pyridine (1.8 mL, 17.9 mmol) was added. The solution stirred 2 h at room temperature and was cooled to 0° C. at which time 6N HCl (18 mL) was slowly added. When the heat of the reaction subsided, the flask was warmed to room temperature and allowed to stir approximately 4 h. The solution was neutralized with solid sodium carbonate and diluted with ethyl acetate and water. The aqueous layer was extracted with ethyl acetate (3×50 mL) and the combined organic extract was washed with brine and dried over MgSO4, filtered and evaporated. Chromatography on silica gel gave 368 mg of recovered oxime and 549 mg (50%) of the desired hydroxylamine intermediate.

e) To a solution of trimethylsilyl isocyanate (0.95 mL, 5.93 mmol) in 5 mL THF at room temperature was added 1-(5-methoxycarbonylfur-2-yl)ethyl hydroxylamine (0.549 mg, 2.97 mmol) in 10 mL of THF with stirring. After 30 min the reaction was quenched with saturated ammonium chloride solution (10 mL). The aqueous layer was saturated with NaCl and extracted with ethyl acetate (3×25 mL). The combined organic extract was dried over MgSO4, filtered and concentrated. Chromatography (silica gel, 5% methanol/ether) yielded 500 mg (74%) of the desired product as a solid foam. The material was taken up in ethyl acetate, hexane was added to the cloud point and the solution was placed in the freezer for an hour to yield white crystals; m.p.=99° C.; 1H NMR (300 MHz, DMSO-d6) 9.18 (bs, 1H), 7.23 (d, J=3.90 Hz, 1H), 6.48 (m, 3H), 5.35 (q, J=12.61, 6.30 Hz, 1H), 3.79 (s, 3H), 1.38 (d, J=7.20 Hz, 3H); MS (M+H)+ =229; Analysis calc'd for $C_9H_{12}N_2O_5$: C, 47.35; H, 5.30; N, 12.28. Found C, 46.66; H, 5.26; N, 12.22.

Example 44

N-hydroxy-N-(1-(5-carboethoxyfur-2-yl)ethyl) urea

The desired material was prepared according to the method of Example 43, except using ethanol in step b) instead of methanol; 1H NMR (300MHz, DMSO-d6) 9.18 (bs, 1H), 7.21 (d, J=3.75 Hz, 1H), 6.49 (bs, 2H), 6.46 (m, 1H), 5.35 (q, J=7.26, 14.4 Hz, 1H), 4.27 (q, J=6.87, 13.81 Hz, 2H), 1.38 (d, J=6.6 Hz, 3H), 1.27 (t, J=6.42 Hz, 3H); MS (M+NH4)+ =260; Analysis calc'd for $C_{10}H_{14}N_2O_5$: C, 49.57; H, 5.83; N, 11.57. Found: C, 48.71; H, 5.15; N, 10.98.

Example 45

N-hydroxy-N-(1-(5-N,N-diethylcarboxamidofur-2-yl)ethyl) urea a) To a solution of 2-acetyl-fur-5-yl carboxylic acid (0.50 g, 3.25 mmol) in 5 mL of THF at 0° C. was added oxalyl chloride (0.30 mL, 3.41 mmol) and N,N-dimethylformamide (25 mL, 0.33 mmol). The solution stirred at 0° C. for 1 h and then diethyl amine (0.67 ml, 0.71 mmol) in 5 mL of THF was added slowly. The solution was warmed to room temperature and allowed to stir overnight. The mixture was quenched with saturated sodium bicarbonate solution and the aqueous layer was extracted with ethyl acetate (3×15 mL). The combined organic extract was washed with 10% HCl (1×20 mL) and brine (1×20 mL), dried over MgSO$_4$, filtered and concentrated to yield 700 mg of 2-acetyl-fur-5-yl N,N-diethylcarboxyamide.

b) The desired product was prepared according to the method of Example 43 starting at step c) using 2-acetyl-fur-5-yl N,N-diethylcarboxyamide instead of 2-acetyl-5-methoxycarbonylfuran. No chromatography was needed to provide pure solid product; m.p.=139° C.; $^1$H NMR (300 MHz, DMSO-d6) 9.15 (bs, 1H), 6.89 (d, J=3.45 Hz, 1H), 6.45 (bs, 2H), 6.35 (d, J=3.30 Hz, 1H), 5.37 (q, J =6.90, 14.65 Hz, 1H), 3.45 (bs, 4H), 1.39 (d, J=6.30 Hz, 3H), 1.16 (bs, 6H); MS (M+H)$^+$=270; Analysis calc'd for C$_{12}$H$_{19}$N$_3$O$_4$: C, 53.50; H, 7.11; N, 15.61. Found: C, 53.05; H, 6.96; N, 15.27.

Example 46

N-hydroxy-N-(1-(5-N-benzylcarboxamidofur-2-yl)ethyl urea

The intermediate, 2-acetyl-fur-5-yl N-benzylcarboxyamide was prepared according to the method of Example 45 except benzylamine was used instead of diethylamine in step a). The desired product was prepared according to the method of Example 43 starting at step c) using 2-acetyl-fur-5-yl N-benzylcarboxyamide instead of 2-acetyl-5-methoxycarbonylfuran. The solid product was collected and washed with ether; m.p.=169° C.; $^1$H NMR (300 MHz, DMSO-d6) 9.13 (bs, 1H), 8.77 (t, J=5.25 Hz, 1H), 7.35-7.20 (m, 5H), 7.05 (d, J=3.02 Hz, 1H), 6.49 (bs, 2H), 6.39 (m, 1H), 5.34 (q, J=6.90, 13.51 Hz, 1H), 4.41 (d, J =6.15 Hz, 2H), 1.38 (d, J=6.45 Hz, 3H); MS (M+NH$_4$)$^+$=321; Analysis calc'd for C$_{15}$H$_{17}$N$_3$O$_4$: C, 59.38; H, 5.65; N, 13.86; Found: C, 58.89; H, 5.55; N, 13.58.

Example 47

N-hydroxy-N-(1-(5-methoxyethoxymethylfur-2-yl)ethyl) urea a) To a solution of furan (10.7 mL, 0.147 mol) in 100 mL of THF at 0° C. was added n-butyllithium (65 mL, 0.149 mol). The reaction was stirred 3 h and was cooled to −78° C. To the reaction flask was then slowly added 2-methoxy-ethoxymethylchloride (16.8 mL, 0.147 mol) in 100 mL THF. The solution was warmed to −20° C. and allowed to stir until the solution was clear. It was then quenched with saturated ammonium chloride solution (50mL) and the aqueous layer was washed with ethyl acetate (3×, 50 mL). The combined organic layer was washed with brine, dried (MgSO$_4$), filtered and evaporated to yield 18 g of crude product. Distillation under high vacuum yielded 14.5 g (63%) of 2-methoxyethoxy-methylfuran.

b) To a solution of diisopropylamine (9.9 mL, 70.5 mmol) in THF (30 mL) at 0° C. was added n-butyllithium (28 mL, 70.5 mmol, 2.5M in hexanes) and the solution was stirred 30 min and then cooled to −78° C. A solution of the furan intermediate from part a). above (10 g, 64.1 mmol) in THF (30 mL) was added slowly. The mixture was stirred for 30 min. and then N-methoxy-N-methylacetamide ( 9.9 g, 96.1 mmol) in THF (20 mL) was added. The solution was quenched with saturated ammonium chloride solution (20mL) and the aqueous layer was extracted with ethyl acetate (3×, 20mL). The combined organics were washed with brine (1×, 20 mL), dried over MgSO$_4$, filtered and evaporated. Chromatography (silica gel, 1:1 ether/hexanes) yielded (2.3 g) of the desired intermediate 2-acetyl-5-methoxyethoxymethylfuran.

c) Following the procedure of example 36 using 2-acetyl-5-methoxyethoxy-methylfuran instead of 2-acetylfuran the corresponding oxime was prepared.

d) Following the procedure of example 36, part b). the oxime was reduced with borane-pyridine to provide the corresponding hydroxylamine intermediate.

e) Following the procedure of example 36, part c). The desired product was obtained. $^1$H NMR (300 MHz, DMSO-d6) 9.06 (bs, 1H), 6.41 (bs, 2H), 6.31 (d, J=3.24 Hz, 1H), 6.18 (d, J=3.24 Hz, 1H), 5.29 (q, J=14.11, 6.84 Hz, 1H), 4.34 (bs, 2H), 3.52 (m, 2H), 3.43 (m, 2H), 3.23 (s, 3H), 1.33 (d, J=6.90 Hz, 3H). MS (M+H)$^+$=259, (M+NH$_4$)$^+$=276. Analysis calc'd for C$_{11}$H$_{18}$N$_2$O$_5$: C, 51.16; H, 7.02; N, 10.85. Found: C, 50.20; H, 6.41; N, 10.60.

Example 48

N-hydroxy-N-(1-(5-ethoxymethylfur-2-yl)methyl) urea

The title compound was prepared by the method of example 47, part a) using ethoxymethylchloride instead of 2-methoxy-ethoxymethylchloride. The final product was recrystallized from ether/hexanes. m.p.=80.5° C.; $^1$H NMR (300 MHz, DMSO-d6) 9.49 (bs, 1H), 6.40 (bs, 2H), 6.32 (d, J=3.0 Hz, 1, 6.21 (d, J=2.97 Hz, 1H), 4.45 (bs, 2h), 4.32 (bs, 2H), 3.44 (q, J=14.65, 7.20 Hz, 2H), 1.11 (t, J=6.30 Hz, 3H). MS (M+NH$_4$)$^+$=232. Analysis calc'd for C$_9$H$_{14}$N$_2$O$_4$: C, 50.44; H, 6.59; N, 13.08. Found: C, 50.37; H, 6.49; N, 13.02.

Example 49

N-hydroxy-N-(1-(5-benzyloxymethylfur-2-yl)ethyl) urea

The title compound was prepared by the method of example 47, part a) using chloromethylbenzylether instead of 2-methoxy-ethoxymethylchloride. The final product crystallized from ethyl acetate, was filtered and washed with ether. m.p.=121° C.; $^1$H NMR (300 MHz, DMSO-d6) 9.06 (bs, 1H), 7.38-7.27 (m, 5H), 6.42 (bs, 2H), 6.35 (d, J =3.02 Hz, 1H), 6.20 (d, J=2.94 Hz, 1H), 5.30 (q, J =13.51, 6.91 Hz, 1H), 4.48 (bs, 2H), 4.40 (bs, 2H), 1.35 (d, J=7.51 Hz, 3H); MS (M+NH$_4$)$^+$=308. Analysis calc'd for C15H18N2O4: C, 62.06; H, 6.25; N, 9.65. Found: C, 61.29; H, 6.26; N, 9.50.

Example 50

N-hydroxy-N-(5-phenylfur-2-yl)methyl) urea a) To a 0° C. solution of furan (10.2 g, 0.15 mol) in 100 mL of THF was added 2.5 M n-butyllithium (60 mL, 0.15 mol). The solution was stirred 3 h and the suspension was then added to a solution of zinc chloride (20 g, 0.15 mol) in 100 mL of THF at room temperature and stirred 1 h. In another flask bromobenzene (10.5 mL, 0.10 mol) was added to a solution of tetrakis(triphenylphosphine)palladium(0) (0.57 g, catalytic) in 300 ml THF and to this mixture was added the furyl zinc solution via cannula. The mixture was heated at 50° C. and stirred for 24 h. The reaction was cooled and quenched with 10% aqueous HCl solution (100 mL). The aqueous layer was washed with ether (2×100 mL) and the combined organic extract was washed with saturated sodium bicarbonate solution (100 mL), brine (100 mL), dried over MgSO$_4$, filtered and concentrated. Distillation at 10 torr (b.p. 94° C.) yielded 12.1 g (81%) of 2-phenylfuran.

b) To a 0° C. solution of N,N-dimethylformamide (1.9 mL, 24.97 mmol) in a three-neck flask equipped with a condenser was added POCl$_3$ (0.65 mL, 6.94 mmol) dropwise via syringe with stirring. When the heat of the reaction subsided, 2-phenylfuran (1.0 g, 6.94 mmol) was added. The reaction was warmed to 80° C. and stirred overnight. The solution was cooled to room temperature and then neutralized to pH 8 with aqueous saturated sodium acetate. The mixture was extracted with ether (3×30 mL), dried over MgSO$_4$, filtered and evaporated. Chromatography (silica gel, 20% ether/hexanes) yielded 1.0 g (83%) of 5-phenyl-2-furaldehyde.

c) Following the procedure of example 36 using 2-formyl-5-phenylfuran instead of 2-acetylfuran the corresponding oxime was prepared.

d) Following the procedure of example 36, part b). the oxime was reduced with borane pyridine to provide N-(5-phenylfur-2-yl)methyl hydroxylamine.

e) Following the procedure of example 36, part c). the desired product was obtained after chromatography (silica gel, ether). m.p.=149° C.; $^1$H NMR (300 MHz, DMSO-d6) 9.48 (bs, 1H), 7.66 (m, 2H), 7.41 (m, 2H), 7.26 (m, 1H), 6.87 (d, J=3.15 Hz, 1H), 6.49 (bs, 1H), 6.39 (d, J=3.30 Hz, 1H), 4.53 (bs, 2H); MS (M+H)$^+$=233, (M+NH$_4$)$^+$=250. Analysis calc'd for C$_{12}$H$_{12}$N$_2$O$_3$: C, 62.05; H, 5.21; N, 12.07. Found: C, 61.74; H, 5.14; N, 11.13.

Example 51

N-hydroxy-N-(5-phenylfur2-yl)methyl-N'-methyl urea

To a solution of N-(5-phenylfur-2-yl)methyl hydroxylamine (0.5 g, 2.64 mmol) in tetrahydrofuran (30 mL) was added methylisocyanate (0.24 mL, 3.97 mmol) dropwise at room temperature under nitrogen while stirring. The reaction was stirred for 20 h and ethyl ether (100 mL) and water (100 mL) was added. The organic layer was separated, washed with saturated aqueous NaCl, dried over MgSO$_4$, filtered and concentrated in vacuo, to give a solid (0.58 g). Purification by chromatography (silica gel, 2% methanol in dichloromethane) gave the desired product (0.28 g), mp 135°-139° C.; NMR (300 MHz, DMSO-d6): 2.63 (3H, d, J=5.4 Hz), 4.53 (2H, s), 6.38 (1H, d, J=3.3 Hz), 6.87 (1H, d, J =3.3 Hz), 7.03 (1H, q, J=5.4 Hz), 7.24-7.30 (1H, m), 7.38-7.45 (2H, m), 7.38-7.45 (2H, m), 7.62-7.68 (2H, m), 9.40 (1H, s); MS (CI-NH$_3$): M+H=247; Analysis Calculated for C$_{13}$H$_{14}$N$_2$O$_3$: C, 63.40; H, 5.73, N, 11.38; Found C, 63.29; H, 5.76; N, 11.34.

Example 52

N-hydroxy-N-(3-fur-3-yl-prop-2-enyl) urea a) To a solution of 2N NaOH (115 mL) was added 3-furaldehyde (4.5 mL, 52.0 mmol) dropwise. The solution was stirred until homogeneous (approximately five minutes) and then cooled to 0° C. and acetaldehyde (1.65 mL, 57.2 mmol) in 5 mL water was added. The reaction was stirred at 0° C. for 30 min and was then diluted with ether. The mixture was separated and the aqueous layer was extracted with ether (3×50 mL). The combined organic extract was washed with brine, dried over MgSO$_4$, filtered and evaporated to yield 4.56 g of crude product. Chromatography (silica gel ,30% ether/hexanes) yielded 2.6 g (41%) of 3-(furan-3-yl)propenal.

b) Following the procedure of example 36 using 3-(furan-3-yl)propenal instead of 2-acetylfuran the corresponding oxime was prepared.

c) The oxime was reduced following the procedure of example 36, part b). except the reaction was not warmed to room temperature after addition of the 6N HCl but instead the solution was stirred about 15 min at 0° C. and then neutralized to provide N-3-(1-fur-3-yl)propenyl hydroxylamine.

d) The desired product was prepared by following the procedure of example 36, part c) except the crude material was not chromatographed but was diluted with ether/hexanes solution and filtered to give a pale yellow solid. m.p.=136°-137° C.; $^1$H NMR (300 MHz, DMSO-d6) 9.30 (bs, 1H), 7.70 (bs, 1H), 7.61 (m, 1H), 6.70 (d, J=3.30 Hz, 1H), 6.42-6.32 (m, 3H), 5.96 (m, 1H), 4.03 (m, 2H); MS (M+H)$^+$=183, (M+NH$_4$)$^+$=200. Analysis calc'd for C$_8$H$_{10}$N$_2$O$_3$: C, 52.73; H, 5.54; N, 15.38. Found: C, 52.39; H, 5.55; N, 15.05.

Example 53

N-hydroxy-N-(3-(5-phenylfur-2-yl)prop-2-enyl) urea a) The procedure of example 52 part a). was followed using 5-phenyl-2-furaldehyde instead of 3-furaldehyde to provide 5-phenyl-3-(furan-2-yl)propenal.

b) Following the procedure of example 36 using 5-phenyl-3-(furan-2-yl)propenal instead of 2-acetylfuran the corresponding oxime was prepared.

c) The oxime was reduced following the procedure of example 36, part b). except the reaction was not warmed to room temperature after addition of the 6N HCl but instead the solution was stirred about 15 min at 0° C. and then neutralized to provide N-3-(1-(5-phenylfur-2-yl))propenyl hydroxylamine.

d) The desired product was prepared by following the procedure of example 36, part c). m.p. 157°-158° C.; $^1$H NMR (300 MHz, DMSO-d6) 9.48 (bs, 1H), 7.73 (m, 2H), 7.43 (m, 2H), 7.29 (m, 1H), 6.97 (d, J=2.94 Hz, 1H), 6.52 (d, J=3.02 Hz, 1H), 6.48-6.38 (m, 3H), 6.26-6.15 (m, 1H), 4.10 (d, J=7.51 Hz, 2H); MS (M+H)$^+$=259. Analysis calc'd for C$_{14}$H$_{14}$N$_2$O$_3$. 65.09; H, 5.47; N, 10.85. Found: C, 63.48; H, 5.32; N, 10.07.

Example 54

N-Hydroxy-N-(2,5-dimethylfur-3-ylmethyl) urea a) To a stirred solution of 3-carbomethoxy-2,5-dimethylfuran (2.5 g, 16.2 mmol) in methylene chloride (distilled from CaH) at −20° C., under N$_2$, was added 2.5 eq of DIBAL (1M in CH$_2$Cl$_2$). After 1 h, the dry ice/acetonitrile bath was removed and 60 mL of 10% HCl was added dropwise. The organic layer was separated, dried over MgSO$_4$, and evaporated. The residue was chromatographed (silica gel, 60% ether/hexane) to yield 1.3 g of 2,5-dimethyl-3- hydroxymethylfuran.

b) To a stirred solution of oxalyl chloride (11.3 mmol) in methylene chloride at −78° C. was added DMSO (20.6 mmol) dropwise. The mixture was stirred for 10 min. then 2,5- dimethyl-3-hydroxymethylfuran (11.3 mmol) was added. The mixture was stirred for 30 min and then triethylamine (55 mmol) was added slowly to the cold mixture. After 1 h the mixture was filtered , evaporated, diluted with THF, filtered again, and used directly in the next step.

c) Following the procedure of example 36 using 2,5-dimethylfuran-3-ylcarboxaldehyde instead of 2-acetylfuran the corresponding oxime was prepared.

d) The oxime was reduced following the procedure of example 36, part b). except 10% HCl was used instead of 6N HCl to provide N-(2,5-dimethylfuran-3-yl)methylhydroxylamine.

e) The desired product was prepared by following the procedure of example 36, part c),the residue was chromatographed (silica gel, 7% MeOH/CH$_2$Cl$_2$) to yield 610 mg of the product. mp. 115°–117° C.; NMR(300MHz, DMSO-d6): 2.16 (6H, s); 4.17 (2H, s); 5.90 (1H, s); 6.26 (2H, brs); 9.18 (1H, s); MS (CI-NH$_3$): M+H=185.

Example 55

N-Hydroxy-N-(1-(2,5-dimethylfur-3-yl)ethyl) urea

The title compound was prepared by the method of example 36 using 3-acetyl-2,5-dimethylfuran instead 2-acetylfuran in an overall yield of 15%. The product was recrystalyzed from EtOAc/Hex. m.p.=145°–146° C.; NMR (300MHz,DMSO-d6) 1.25 (3H,d, J=7.5Hz), 2.26 (6H,S), 5.09 (1H,q,J=7.5Hz), 6.00 (1H,s), 6.23 (2H,br s), 8.95 (1H,s); MS (CI-NH$_3$): M+H=199

Example 56

N-Hydroxy-N-(1-fur-3-ylethyl) urea a) To a stirred solution of 3-furaldehyde (5.6 g, 58 mmol) in tetrahydrofuran (75 mL) at 0° C. was added a solution of CH$_3$MgBr in ether (64 mL. of 3M, 64 mmol). After 30 min saturated aqueous NH$_4$Cl was added and the pH was adjusted to 7 with 10% aqueous HCl. The organic layer was separated and the aqueous phase was extracted with ether. The combined organic layers were washed with brine, dried over MgSO$_4$, filtered and concentrated to give a yellow liquid (5.6 g) which was used directly in the next step.

b) To a solution of oxalyl chloride (7.3 g, 57 mmol) in dichloromethane (50 mL) at −78° C. was added DMSO (8.9 g, 114 mmol). The mixture was stirred for 15 min. then a solution of the crude alcohol from part a). in dichloromethane (25 mL) was added dropwise. The reaction was stirred for 30 min. at −78° C. and then triethylamine (26 g, 260 mmol) was added to the reaction mixture and the mixture was allowed to warm slowly to room temperature. The mixture was concentrated and the residue was takenup in ether and filtered through a pad of Celite. The solids were washed with ether and the combined ether filtrate was washed with water, brine, dried over MgSO$_4$, filtered and concentrated to give a solid (4.0 g) which was purified by chromatography (silica gel, 1:1 ether, hexane) to provide 3-acetylfuran (2.9 g). The above process was repeated to provide further material.

c) A mixture of 3-acetylfuran (3.6 g, 27 mmol), hydoxylamine hydrochloride (3.4 g, 50 mmol) and pyridine (5.2 g, 66 mmol) and ethanol (50 mL) was heated at 50° C. for 1 h. The ethanol was evaporated and the residue was partitioned between ethyl acetate and water. The aqueous phase was extracted with ethyl acetate. The combined organic extract was washed with 10% HCl and brine, dried over MgSO$_4$, filtered and concentrated to give the corresponding oxime (3.4 g) which was used in the next step.

d) To a solution of the oxime from part c). in ethanol (200 mL) was added borane:pyridine complex (8.4 g, 90 mmol) and the mixture was stirred for 15 min. Then 6N HCl (90 mL) was added dropwise and an exothermic reaction with gas evolution occurred. After about 1 h the ethanol was evaporated and the residue was made basic with 2N NaOH. The aqueous solution was extracted with ethyl acetate twice and the combined extract was washed with brine, dried over MgSO$_4$, filtered and concentrated to give a solid (3.4 g). Purification by chromatography (silica gel, ethyl acetate) gave the desired hydroxylamine intermediate (2.2 g). which was used directly in the next step.

e) To a solution of the hydroxylamine from part d). (2.2 g, 17 mmol) in tetrahydrofuran (50 mL) was added dropwise trimethylsilylisocyanate (3.9 g, 34 mmol). After stirring at room temperature for 1 h the mixture was heated to reflux for 1 h. After cooling a saturated aqueous solution of NH$_4$Cl was added and the mixture was extracted twice with ethyl acetate. The combined organic extract was washed with brine, dried over MgSO$_4$, filtered and concentrated to give a white solid. Trituration with ether and filtration gave the desired product (1.9 g). m.p. 128-°130° C.; $^1$H NMR (300 MHz, DMSO-d6) 1.31 (3H, d, J=7.5 Hz), 5.17 (1H, m), 6.35 (2H, bs), 6.39 (1H, m), 7.5 (1H, m), 7.54 (1H, m), 8.98 (1H, s); MS (M+H)$^+$=171. Analysis calc'd for C$_7$H$_{10}$N$_2$O$_3$. C, 49.41; H, 5.92; N, 16.46. Found: C, 49.28; H, 5.97; N, 16.38.

Example 57

N-Hydroxy-N-(1-(5-pyrid-2-ylfur-2-yl)ethyl) urea a) To a solution of furan (5.0 g, 73 mmol) in tetrahydrofuran (THF, 75 mL) at 0° C. was added dropwise a solution of nBuLi (29 mL of 2.5 M in hexane, 73 mmol) and the mixture was stirred for 3 h and then transferred via a cannula into a stirred solution of anhydrous ZnCl$_2$ (9.9 g, 73 mmol) in THF (75 mL). After stirring for 1 h at room temperature this solution was added dropwise via a cannula to a stirred solution of 2-bromopyridine (7.7 g, 49 mmol) and a catalytic amount of Pd(P(C$_6$H$_5$)$_3$)$_4$ (0.28 g, 0.24 mmol) in THF (100 mL). After stirring for 24 h, a saturated aqueous solution of NH$_4$Cl (10 mL) was added and the solvent was evaporated. The residue was taken up in water and ether, the layers were separated and the aqueous phase was extracted with ether. The combined ether extract was washed with brine, dried over MgSO$_4$, filtered and concentrated to give after purification by chromatography (silica gel, 1:1 ether, hexane) 2-(2-furyl)pyridine (6.5 g).

b) To a solution of 2-(2-furyl)pyridine (6.5 g, 45 mmol) in ether (250 mL) at −78° C. was added a solution of nBuLi (19 mL of 2.5 M in hexane, 47 mmol). The mixture was stirred for 1 h at −78° C. and 1,5 h at 0° C. after which as solution of N-methoxy-N-methylacetamide (4.6 g, 45 mmol) in ether (25 mL) was added dropwise and the mixture was stirred for 3 days at room temperature. Aqueous NH$_4$Cl was added and the layers were separated. The aqueous phase was extracted with ethyl acetate and the combined organic layers were washed with water, brine, dried over MgSO$_4$, filtered and concentrated to give after purification by chromatography (silica gel, 1:1 ethyl acetate, hexane) 2-(5-acetyl-2- furyl)pyridine (3.5 g).

c) The intermediate from part b) was converted according to the method of Example 36 parts a)–c) to the desired titled example. m.p. 185°–187° C. (dec); $^1$H NMR (300 MHz, DMSO-d6) 1.43 (3H, d, J=7.5 Hz), 5.39 (1H, m) 6.41 (1H, m), 6.48 (2H, bs), 7.0 (1H, d, J=3.0 Hz), 7.26 (1H, m), 7.64 (1H, m), 7.84 (1H, m), 8.55 (1H, m), 9.14 (1H, s); MS (M+H)$^+$=248. Analysis calcd. for C$_{12}$H$_{13}$N$_3$O$_3$½H$_2$O. C, 56.24; H, 5.51; N, 16.40. Found: C, 56.69; H, 5.27; N, 16.30.

Example 58

N-Hydroxy-N-(fur-2-ylmethyl) urea

The desired product was prepared according to the method of Example 36 using 2-furancarboxaldehyde instead of 2- acetylfuran. m.p. 128°–131° C.; $^1$H NMR (300 MHz, DMSO-d6) 4.48 (2H, s), 6.27 (1H, m), 6.4 (3H, m), 7.57 (1H, m), 9.39 (1H, s); MS (M+H)$^+$ = 157. Analysis calc'd for $C_6H_8N_2O_3$. C, 46.15; H, 5.16; N, 17.94. Found: C, 46.38; H, 5.28; N, 17.79.

Example 59

N-hydroxy-N-3-(5-methylfur-2-yl)prop-2-enyl)urea a) 5-Methylfurfural (10 g, 91 mmol) was added dropwise to 2N NaOH (200 mL) and the mixture was stirred for 30 min. A solution of acetaldehyde (8.0 g, 182 mmol) in water (20 mL) was added to the above mixture. After stirring for 3 h the mixture was extracted twice with ether and the combined ether extract was washed with brine, dried over MgSO$_4$, filtered and concentrated to give after distillation (collected bp 65°–85° C.) 3-(5-methylfur-2-yl)-propenal (5.5 g).

b) The aldehyde from part a). was converted according to the method of example 36 parts a)–c) to the desired titled compound. m.p. 131°–133° C.; $^1$H NMR (300 MHz, DMSO-d6) 2.28 (3H, s), 4.03 (2H, d, J=7.5 Hz), 5.95 (1H, m), 6.07 (1H, m), 6.24 (1H, m), 6.33 (1H, d, J=16 Hz), 6.37 (2H, bs), 9.30 (1H, s); MS (M+H)> =197. Analysis calc'd for $C_9H_{12}N_2O_3$. C, 55.09; H, 6.16; N, 14.28. Found: C, 54.77; H, 6.16; N, 14.08.

Example 60

N-hydroxy-N-((1-methyl)-3-(5-methylfur-2-yl)prop-2-enyl) urea a) To a solution of 5-methylfurfural (2.0 g, 18 mmol) in toluene (50 mL) was added (C$_6$H$_5$)3P=CHCOCH$_3$ (6.1 g, 19 mmol) and the mixture was stirred at reflux for 18 h. The mixture was cooled and filtered through silica gel and washed with 1:1 ether, hexane. The filtrate was concentrated and purified by chromatography (silica gel, 40% ether in hexane) to give 1-(5-methylfur-2-yl)-buten-3-one.

b) The ketone from part a). was converted according to the method of example 36 parts a).–c). to the desired titled compound. m.p. 122°–124° C.; $^1$H NMR (300 MHz, DMSO-d6) 1.19 (3H, d, J=7.5 Hz), 2.26 (3H, s), 4.74 (1H, m), 6.01 (1H, m), 6.06 (1H, m), 6.25 (2H, m), 6.36 (2H, m), 9.0 (1H, s); MS (M+H)$^+$ =211.

The compounds of the following Examples, wherein R$_1$=NH$_2$, A=2—(—CH(CH$_3$)—), X=O, M=H and Y is as indicated below, can be prepared by methods analogous to those described in Example 2 and by substituting the appropriate arylhalide for bromobenzene in step a) of Example 2.

| Example | Y |
|---|---|
| 61 | 5-(2-methylpyrid-2-yl) |
| 62 | 5-(pyrid-3-yl) |
| 63 | 5-(pyrid-4-yl) |
| 64 | 5-(2,5-dimethylthien-3-yl) |
| 65 | 5-(5-methylthien-2-yl) |
| 66 | 5-(5-methylfur-2-yl) |
| 67 | 5-(thiazol-2-yl) |
| 68 | 5-(pyrimid-2-yl) |
| 69 | 5-(4-methoxyphenyl) |
| 70 | 5-(4-chlorophenyl) |
| 71 | 5-(4-carbomethoxyphenyl) |
| 72 | 5-(4-cyanophenyl) |
| 73 | 5-(4-fluorophenyl) |

The compounds of the following Examples, wherein R$_1$=NH$_2$, A=2—(—CH$_2$—), X=O, M=H and Y is as indicated below, can be prepared by methods analogous to those described in Example 50 and by substituting the appropriate arylhalide for bromobenzene in step a) of Example 50.

| Example | Y |
|---|---|
| 74 | 5-(pyrid-2-yl) |
| 75 | 5-(pyrid-3-yl) |
| 76 | 5-(pyrid-4-yl) |
| 77 | 5-(2-methylpyrid-3-yl) |
| 78 | 5-(5-methoxypyrid-3-yl) |
| 79 | 5-(N-methylindol-2-yl) |
| 80 | 5-(thiazol-2-yl) |
| 81 | 5-(pyrimid-2-yl) |
| 82 | 5-(4-methoxyphenyl) |
| 83 | 5-(4-chlorophenyl) |
| 84 | 5-(4-carbomethoxyphenyl) |
| 85 | 5-(4-cyanophenyl) |
| 86 | 5-(4-fluorophenyl) |

The compounds of the following Examples, wherein R$_1$=CH$_3$, A=2—(—CH(CH$_3$)—), X=O, M=H and Y is as indicated below, can be prepared by methods analogous to Example 2 and by substituting the appropriate arylhalide for mobenzene in step a) of Example 2. This provides a hydroxylamine which is then converted to the corresponding N-hydroxyacetamide acetamide according to method described in Example 4.

| Example | Y |
|---|---|
| 87 | 5-(2-methylpyrid-2-yl) |
| 88 | 5-(pyrid-3-yl) |
| 89 | 5-(pyrid-4-yl) |
| 90 | 5-(2,5-dimethylthien-3-yl) |
| 91 | 5-(5-methylthien-2-yl) |
| 92 | 5-(5-methylfur-2-yl) |
| 93 | 5-(thiazol-2-yl) |
| 94 | 5-(pyrimid-2-yl) |
| 95 | 5-(4-methoxyphenyl) |
| 96 | 5-(4-chlorophenyl) |
| 97 | 5-(4-carbomethoxyphenyl) |
| 98 | 5-(4-cyanophenyl) |
| 99 | 5-(4-fluorophenyl) |

The compounds of the following Examples, wherein R$_1$=CH$_3$, A=2—(—CH$_2$—), X=O, M=H and Y is as indicated below, can be prepared by methods analogous to Example 50 and by substituting the appropriate arylhalide for bromobenzene in step a) of Example 50. This provides a hydroxylamine which is then converted to the corresponding N-hydroxyacetamide acetamide according to method described in Example 4.

| Example | Y |
|---|---|
| 100 | 5-(pyrid-2-yl) |
| 101 | 5-(pyrid-3-yl) |
| 102 | 5-(pyrid-4-yl) |
| 103 | 5-(2-methylpyrid-3-yl) |
| 104 | 5-(5-methoxypyrid-3-yl) |
| 105 | 5-(indol-2-yl) |
| 106 | 5-(thiazol-2-yl) |
| 107 | 5-(pyrimid-2-yl) |

-continued

| Example | Y |
|---------|---|
| 108 | 5-(4-methoxyphenyl) |
| 109 | 5-(4-chlorophenyl) |
| 110 | 5-(4-carbomethoxyphenyl) |
| 111 | 5-(4-cyanophenyl) |
| 112 | 5-(4-fluorophenyl) |

The compounds of the following Examples, wherein $R_1=NH_2$, $A=2—(—CH(CH_3)—)$, $X=O$, $M=H$ and Y is as indicated below, can be prepared by methods analogous to Example 5 and by substituting the appropriate arylmethylphosphonate for diethyl benylphosphonate in step a) of Example 5.

| Example | Y |
|---------|---|
| 113 | 5-(—CH=CH-pyrid-2-yl) |
| 114 | 5-(—CH=CH-pyrid-3-yl) |
| 115 | 5-(—CH=CH-pyrid-4-yl) |
| 116 | 5-(CH=CH-5-methylthien-2-yl) |
| 117 | 5-(—CH=CH-2,5-dimethylthien-3-yl) |
| 118 | 5-(—CH=CH-5-methylfur-2-yl) |
| 119 | 5-(—CH=CH-2,5-dimethylfur-3-yl) |
| 120 | 5-(—CH=CH-3,4,5-trimethoxyphenyl) |
| 121 | 5-(—CH=CH-4-methoxyphenyl) |
| 122 | 5-(—CH=CH-4-carbomethoxyphenyl) |
| 123 | 5-(—CH=CH-4-cyanophenyl) |
| 124 | 5-(—CH=CH-4-chlorophenyl) |
| 125 | 5-(—CH=CH-4-fluorophenyl) |

The compounds of the following Examples, wherein $R_1=NH_2$ or $CH_3$, $A=2—(—CH=CH—CH_2—)$ or $2—(—CH=CH(CH_3)—)$, $X=O$, $M=H$ and Y is as indicated below, can be prepared by methods analogous to those described in Examples 2, 4, 50, 59 and 60.

| Example | Y |
|---------|---|
| 126 | 5-(pyrid-2-yl) |
| 127 | 5-(pyrid-3-yl) |
| 128 | 5-(pyrid-4-yl) |
| 129 | 5-(2-methylpyrid-3-yl) |
| 130 | 5-(5-methoxypyrid-3-yl) |
| 131 | 5-(N-methylindol-2-yl) |
| 132 | 5-(thiazol-2-yl) |
| 133 | 5-(pyrimid-2-yl) |
| 134 | 5-((4-methoxyphenyl) |
| 135 | 5-(4-chlorophenyl) |
| 136 | 5-(4-carbomethoxyphenyl) |
| 137 | 5-(4-cyanophenyl) |
| 138 | 5-(4-fluorophenyl) |

The compounds of the following Examples, wherein $R_1=NH_2$, $A=2—(—CH(CH)_3—)$, $X=O$, $M=H$ and Y is as indicated below, can be prepared by methods analogous to those described in Example 47.

| Example | Y |
|---------|---|
| 139 | 5-(—CH$_2$OCH$_2$-pyrid-2-yl) |
| 140 | 5-(—CH$_2$OCH$_2$-pyrid-3-yl) |
| 141 | 5-(—CH$_2$OCH$_2$-pyrid-4-yl) |
| 142 | 5-(—CH$_2$OCH$_2$-(4-methoxyphenyl)) |
| 143 | 5-(—CH$_2$OCH$_2$-(4-chlorophenyl)) |
| 144 | 5-(—CH$_2$OCH$_2$-(4-carbomethoxyphenyl)) |
| 145 | 5-(—CH$_2$OCH$_2$-(4-cyanophenyl)) |
| 146 | 5-(—CH$_2$OCH$_2$-(4-fluorophenyl)) |

The compounds of the following Examples, wherein $R_1=NH_2$, $A=2—(—CH=CH—CH(CH_3)—)$, $X=O$, $M=H$ and Y is as indicated below, can be prepared by methods assigned analogous to those described in Example 47 and 60.

| Example | Y |
|---------|---|
| 147 | 5-(—CH$_2$OCH$_2$-pyrid-2-yl) |
| 148 | 5-(—CH$_2$OCH$_2$-pyrid-3-yl) |
| 149 | 5-(—CH$_2$OCH$_2$-pyrid-4-yl) |
| 150 | 5-(—CH$_2$OCH$_2$-(4-methoxyphenyl)) |
| 151 | 5-(—CH$_2$OCH$_2$-(4-chlorophenyl)) |
| 152 | 5-(—CH$_2$OCH$_2$-(4-carbomethoxyphenyl)) |
| 153 | 5-(—CH$_2$OCH$_2$-(4-cyanophenyl)) |
| 154 | 5-(—CH$_2$OCH$_2$-(4-fluorophenyl)) |

The compounds of the following Examples, wherein $R_1=NH_2$, $A=2—(—CH(CH_3)—)$, $X=NR_4$ wherein $R_4$ is indicated below, $M=H$ and Y is as indicated below, can be prepared by methods analogous to those described in Example 8.

| Example | Y | R$_4$ |
|---------|---|-------|
| 155 | 5-(4-fluorophenyl) | —CH$_2$-(4-chlorophenyl) |
| 156 | 5-(pyrid-3-yl) | —CH$_2$-(4-chlorophenyl) |
| 157 | 5-(pyrid-4-yl) | —CH$_2$-(4-chlorophenyl) |
| 158 | 5-(pyrid-2-yl) | methyl |
| 159 | 5-(4-chlorophenyl) | methyl |
| 160 | 5-(4-carbomethoxyphenyl) | methyl |
| 161 | 5-(4-chlorophenyl) | —CH$_2$-pyrid-4-yl |

Inhibition of 5-Lipoxygenase

Inhibition of 5-lipoxygenase activity was determined using the 20,000× g supernatant from homogenized RBL-1 cells in a similar manner to that described by Dyer and coworkers (Dyer, R. D.; Haviv, F.; Hanel, A. M.; Bornemier, D. A.; Carter, G. W. *Fed. Proc., Fed. Am. Soc. Exp. Biol.* 1984, 43, 1462A). Inhibitory potencies for representative examples of this invention are listed in Table 1. IC$_{50}$ values (concentration of compound producing 50% enzyme inhibition) were calculated by linear regression analysis of percentage inhibition versus log inhibitor concentration plots.

TABLE 1

In vitro 5-lipoxygenase inhibitory potency of representative compounds of this invention.

| Example | IC$_{50}$ (uM) |
|---------|----------------|
| 1 | 12 |
| 2 | 0.54 |
| 3 | 0.70 |
| 4 | 0.51 |
| 5 | 0.30 |
| 6 | 0.33 |
| 7 | 18 |
| 9 | 14 |
| 10 | 19 |
| 11 | 24 |
| 12 | 0.3 |
| 13 | 1.2 |
| 36 | 24 |
| 37 | 11 |
| 39 | 0.9 |
| 40 | 0.4 |
| 41 | 3.5 |
| 43 | 13 |
| 49 | 1.1 |
| 50 | 0.45 |
| 51 | 1.3 |
| 52 | 4.5 |

TABLE 1-continued

In vitro 5-lipoxygenase inhibitory potency of representative compounds of this invention.

| Example | IC$_{50}$ (uM) |
|---|---|
| 53 | 0.19 |
| 54 | 4.0 |
| 55 | 2.9 |
| 56 | 15 |
| 57 | 6.4 |
| 59 | 2.0 |
| 60 | 1.2 |

The results of the assay indicate that the compounds are inhibitors of 5-lipoxygenase.

Inhibition of Leukotriene Biosynthesis

Inhibition of the biosynthesis of leukotrienes in vivo after intraperitoneal administration of compound was determined using a rat peritoneal anaphylaxis model. In this model rats were injected intraperitoneally (ip) with rabbit antibody to bovine serum albumin (BSA) and three hours later injected i.p. with BSA to induce an antigen-antibody response. Rats were sacrificed 15 minutes after this challenge and the peritoneal fluids were collected and analyzed for leukotriene levels. Test compound was administered by oral gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results for representative examples of this invention are shown in Table 2.

TABLE 2

In vivo inhibition of leukotriene biosynthesis by representative compounds of this invention.

| Example | % Inhibition with 200 umol/kg Oral Dose |
|---|---|
| 1 | 84 |
| 2 | 96 |
| 3 | 92 |
| 4 | 87 |
| 5 | 89 |
| 6 | 81 |
| 9 | 91 |
| 11 | 90 |
| 12 | 91 |
| 36 | 57 |
| 43 | 49 |
| 49 | 98 |
| 50 | 78 |
| 52 | 92 |
| 53 | 89 |
| 55 | 66 |
| 56 | 78 |
| 57 | 75 |
| 59 | 94 | the foregoing is merely illustrative of the invention and is not intended to limit the invention to the disclosed compounds. Variations and changes which are obvious to one skilled in the art are intended to be within the scope of and nature of the invention which are defined in the appended claims.

What is claimed is:

1. A compound of the formula

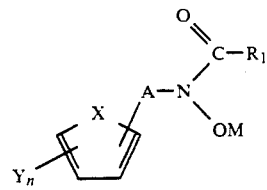

wherein
R$_1$ is selected from
C$_2$ to C$_4$ alkyl,
C$_2$ to C$_4$ alkenyl, and
—NR$_2$R$_3$ where R$_2$ and R$_3$ are independently selected from
hydrogen,
C$_1$ to C$_4$ alkyl,
hydroxyl, and
an aryl group selected from substituted or unsubstituted
phenyl,
1- or 2-naphthyl, and
fluorenyl;
the substituents selected from
halo,
nitro,
cyano,
C$_1$ to C$_4$ alkyl,
alkoxy,
halosubstituted alkyl,
alkoxycarbonyl,
aminocarbonyl,
alkylaminocarbonyl,
dialkylaminocarbonyl, and
alkylsulfonyl;
with the proviso that R$_2$ and R$_3$ are not both hydroxyl;
X is oxygen or NR$_4$ wherein R$_4$ is selected from
hydrogen,
C$_1$ to C$_6$ alkyl,
C$_1$ to C$_6$ alkoxyl,
arylalkyl wherein the aryl portion is as defined above;
A is selected from C$_1$ to C$_6$ alkylene ands C$_2$ to C$_6$ alkenylene;
n is 0, 1, 2, or 3;
Y is selected independently at each occurrence from
hydrogen,
halogen,
hydroxy,
cyano,
halosubstituted alkyl,
C$_1$ to C$_{12}$ alkyl,
C$_2$ to C$_{12}$ alkenyl,
C$_1$ to C$_{12}$ alkoxyl,
C$_3$ to C$_8$ cycloalkyl,
aryl as defined above,
aryloxy wherein the aryl portion is as defined above,
aroyl as defined above;
C$_1$ to C$_{12}$ arylalkyl wherein the aryl portion is as defined above,
C$_1$ to C$_{12}$ arylalkoxy wherein the aryl portion is as defined above,
C$_1$ to C$_{12}$ arylthioalkoxy wherein the aryl portion is as defined above,
alkoxycarbonyl, arylalkoxycarbonyl wherein the aryl portion is as defined above,
aminocarbonyl,
alkylaminocarbonyl,
dialkylaminocarbonyl,
arylalkylamino or wherein the aryl portion is as defined above,
alkoxyalkoxyalkyl,
arylalkoxyalkyl wherein the aryl portion is as defined above,
arylthioalkoxyalkyl wherein the aryl portion is as defined above,
substituted aryl, aryloxy, aroyl, arylalkyl, arylalkenyl, arylalkoxy, arylthioalkoxy, arylalkoxyalkyl, or arylthioalkoxyalkyl, as defined above,
wherein the substituents are selected from
halo,
nitro,
cyano,
$C_1$ to $C_{12}$ alkyl, alkoxy, and halosubstituted alkyl;
the groups(s) Y may be substituted from any of the positions on the ring; and
M is hydrogen, a pharmaceutically acceptable cation, aroyl as defined above, or $C_1$ to $C_{12}$ alkoyl.

2. The compound of claim 1 wherein $R_1$ is —$CH_3$ or —$NH_2$ and X is oxygen.

3. The compound of claim 1 wherein $R_1$ is —$CH_3$ or —$NH_2$ and X is $NR_4$ wherein $R_4$ is hydrogen, $C_1$ to $C_6$ alkyl, $C_1$ to $C_6$ alkoxl, arylalkyl or aroyl as defined therein.

4. The compound of claim 1 wherein A is —CH(CH$_3$)—, —CH$_2$—, —CH=CH—CH$_2$— or —CH=CH—CH(CH$_3$)—.

5. A compound selected from:
N-hydroxy-N-(1-(5-methylfur-2-yl)ethyl) urea;
N-hydroxy-N-(1-(5-phenylfur-2-yl)ethyl) urea;
N-hydroxy-N-(1-(5-phenylfur-2-yl)ethyl)-N'-methyl urea;
N-hydroxy-N-(1-(5-phenylfur-2-yl)ethyl) acetamide;
N-hydroxy-N-(1-(5-(2-phenylethenyl)fur-2-yl)ethyl) urea;
N-hydroxy-N-(1-(5-(2-phenylethenyl)fur-2-yl)ethyl)-N'-methyl urea;
N-hydroxy-N-(5-(2,4,6-trimethoxyphenyl)-fur-2-ylethyl) urea;
N-hydroxy-N-(1-(5-benzyloxymethylfur-2-yl)ethyl) urea;
N-hydroxy-N-(5-phenylfur-2-ylmethyl) urea;
N-hydroxy-N-(3-fur-3-ylprop-2-enyl) urea
N-hydroxy-N-(3-(5-phenylfur-2-yl)prop-2-enyl) urea;
N-hydroxy-N-(1-fur 3-ylethyl) urea;
N-hydroxy-N-3-(1-(5-methylfur-2-yl)propenyl) urea; and
N-hydroxy-N-((1-methyl)-3-(5-methylfur-2-yl)prop-2-enyl) urea.

6. N-hydroxy-N-(1-fur-3-ylethyl) urea.

7. A method for inhibiting 5- and/or 12-lipoxygenase activity or inhibiting leukotriene biosynthesis comprising administering to a mammal in need of such treatment a therapeutically effective amount of a compound of claim 1.

8. A method for inhibiting 5- and/or 12-lipoxygenase activity or inhibiting leukotriene biosynthesis comprising administering to a mammal in need of such treatment a therapeutically effective amount of N-hydroxy-N-(1-fur-3-ylethyl) urea.

9. A pharmaceutical composition for inhibiting 5- and/or 12- lipoxygenase or inhibiting leukotriene biosynthesis, comprising a pharmaceutical carrier and a therapeutically effective amount of a compound of claim 1.

10. A pharmaceutical composition for inhibiting 5- and/or 12- lipoxygenase or inhibiting leukotriene biosynthesis, comprising a pharmaceutical carrier and a therapeutically effective amount of N-hydroxy-N-(1-fur-3-ylethyl) urea.

* * * * *